US012738362B2

(12) United States Patent
Lee et al.

(10) Patent No.: US 12,738,362 B2
(45) Date of Patent: Sep. 15, 2026

(54) JOINT DYNAMIC CAUSAL MODELING AND BIOPHYSICS MODELING TO ENABLE MULTI-SCALE BRAIN NETWORK FUNCTION MODELING

(71) Applicant: The Board of Trustees of the Leland Stanford Junior University, Stanford, CA (US)

(72) Inventors: Jin Hyung Lee, Redwood City, CA (US); Qin Liu, Redwood City, CA (US); Onur Cezmi Mutlu, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 962 days.

(21) Appl. No.: 17/765,259

(22) PCT Filed: Sep. 30, 2020

(86) PCT No.: PCT/US2020/053581

§ 371 (c)(1),
(2) Date: Mar. 30, 2022

(87) PCT Pub. No.: WO2021/067464

PCT Pub. Date: Apr. 8, 2021

(65) Prior Publication Data

US 2022/0359060 A1 Nov. 10, 2022

Related U.S. Application Data

(60) Provisional application No. 62/908,925, filed on Oct. 1, 2019.

(51) Int. Cl.
*G16H 30/20* (2018.01)
*A61B 5/00* (2006.01)
(Continued)

(52) U.S. Cl.
CPC ............ *G16H 30/20* (2018.01); *A61B 5/055* (2013.01); *A61B 5/377* (2021.01); *A61B 5/4064* (2013.01); *A61B 5/4848* (2013.01); *A61B 5/7264* (2013.01)

(58) Field of Classification Search
None
See application file for complete search history.

(56) References Cited

U.S. PATENT DOCUMENTS

2006/0217781 A1 9/2006 John
2011/0022548 A1 1/2011 Shahaf et al.
2012/0232376 A1 * 9/2012 Crevecoeur ............ G16H 50/50 600/509
2015/0088024 A1 3/2015 Sackellares et al.
(Continued)

FOREIGN PATENT DOCUMENTS

CN 106709244 A 5/2017
KR 10-2018-0107224 A 10/2018

OTHER PUBLICATIONS

Ritter et. al. "The Virtual Brain Integrates Computational Modeling and Multimodal Neuroimaging", published by Sage Journals on Apr. 1, 2013, pp. 121-145 (Year: 2013).*
(Continued)

*Primary Examiner* — Jason M Sims
*Assistant Examiner* — Matthew Eric Ogles
(74) *Attorney, Agent, or Firm* — Brian E. Davy; Bozicevic, Field & Francis LLP

(57) ABSTRACT

Methods, systems, and devices, including computer programs encoded on a computer storage medium are provided for combined dynamic causal modeling and biophysics modeling of brain function. In particular, the disclosed methods of modeling brain function can be used to integrate brain function measurements by two or more methods, such as functional neuroimaging and electrophysiology. Sequen-
(Continued)

tial model fitting is used to improve modeling accuracy to generate a more comprehensive model of brain neuronal circuitry.

10 Claims, 10 Drawing Sheets

(51) Int. Cl.
*A61B 5/055* (2006.01)
*A61B 5/377* (2021.01)

(56) References Cited

U.S. PATENT DOCUMENTS

| | | | | |
|---|---|---|---|---|
| 2015/0206051 | A1 | 7/2015 | McIntosh et al. | |
| 2015/0366482 | A1 | 12/2015 | Lee | |
| 2018/0368720 | A1* | 12/2018 | Lee | A61B 5/055 |
| 2019/0206057 | A1 | 7/2019 | Cranmer et al. | |
| 2019/0251450 | A1* | 8/2019 | McIntosh | G06N 3/049 |

OTHER PUBLICATIONS

Hill et. al. "Modeling Sleep and Wakefulness in the Thalamocortical System" Published by the Journal of Neurophysiology 2005, pp. 1671-1698 (Year: 2005).*

Sokolov et al., (2018) "Linking structural and effective brain connectivity: structurally informed Parametric Empirical Bayes (si-PEB)", Brain Structure and Function, 224:205-217.

Bernal-Casas et al. (2017) Studying brain circuit function with dynamic causal modeling for optogenetic fmri. Neuron 93(3):522-532.

Friston et al. (2003) Dynamic causal modelling. Neuroimage 19(4): 1273-1302.

Friston et al. (2014) A DCM for resting state fMRI. NeuroImage 94:396-407.

Park et al. (2018) Dynamic effective connectivity in resting state fMRI. NeuroImage 180:594-608.

Li et al. (2011) Generalised filtering and stochastic DCM for fMRI. NeuroImage 58(2):442-457.

Marreiros et al. (2008) Dynamic causal modelling for fMRI: a two-state model. Neuroimage 39(1):269-78.

Stephan et al. (2008) Nonlinear dynamic causal models for fmri. Neuroimage 42(2):649-662.

Sanchez-Todo et al., (2018) "Personalization of hybrid brain models from neuroimaging and electrophysiology data", BioRxiv, pp. 1-35.

Breakspear, (2017) "Dynamic models of large-scale brain activity", Nature Neuroscience, 20(3):340-352.

Park et al., (2013) "Structural and Functional Brain Networks: From Connections to Cognition", Science, 342:1238411-1-1238411-8.

* cited by examiner

JOINT DYNAMIC CAUSAL MODELING AND BIOPHYSICS MODELING TO ENABLE MULTI-SCALE BRAIN NETWORK FUNCTION MODELING

STATEMENT REGARDING FEDERALLY SPONSORED RESEARCH OR DEVELOPMENT

This invention was made with Government support under contracts MH114227 and NS091461 awarded by the National Institutes of Health. The Government has certain rights in the invention.

BACKGROUND OF THE INVENTION

Brain functions are studied using many different experimental technologies with different spatio-temporal sampling rates and contrast. Some of the modalities utilized include functional magnetic resonance imaging (fMRI), electrophysiology, and optical imaging. Because different technologies offer unique advantages in terms of their ability to probe brain function at different scales while none of them provide a full picture, it would be helpful to find an approach that would allow the different measurements to be utilized together to construct a comprehensive model of brain function.

SUMMARY OF THE INVENTION

Methods, systems, and devices, including computer programs encoded on a computer storage medium are provided for combined dynamic causal modeling and biophysics modeling of brain function. In particular, the methods can be used to integrate brain function measurements by two or more methods, such as functional neuroimaging and electrophysiology. Sequential model fitting is used to improve modeling accuracy to generate a more comprehensive model of brain neuronal circuitry.

In one aspect, a method of modeling brain function is provided, the method comprising a) performing functional neuroimaging of neural activity in one or more regions of interest in a brain of a subject; b) acquiring experimental electrophysiology data for one or more neurons in said one or more regions of interest in the brain of the subject; c) fitting functional neuroimaging data of the neural activity to a dynamic causal model (DCM); d) calculating neural inter-regional and intra-regional connectivity strength estimates from the dynamic causal model; e) generating a biophysics model that simulates synthetic electrophysiology data using the inter-regional and intra-regional connectivity strength estimates; f) comparing the synthetic electrophysiology data to the experimental electrophysiology data; and g) adjusting the biophysical model iteratively until model convergence is reached with the experimental electrophysiology data.

Exemplary functional neuroimaging techniques that can be used in the practice of the subject methods include, without limitation, functional magnetic resonance imaging (fMRI), positron emission tomography (PET), functional near-infrared spectroscopy (fNIRS), single-photon emission computed tomography (SPECT), and functional ultrasound imaging (fUS). In some embodiments, fMRI is used to detect blood oxygen-level dependent (BOLD) signals.

Exemplary electrophysiology techniques that can be used in the practice of the subject methods include, without limitation, electroencephalography (EEG), magnetoencephalography (MEG), and patch-clamping.

In certain embodiments, the method further comprises using optogenetics to excite or inhibit one or more selected neurons of interest using light. In some embodiments, the fMRI experimental data is optogenetic fMRI (ofMRI) experimental data.

Brain function may be modeled by the present methods for any region or regions of the brain. In certain embodiments, the one or more brain regions of interest are in the cerebrum, cerebellum, or brainstem regions of the brain. Brain regions of interest may include, without limitation, the basal ganglia, striatum, medulla, pons, midbrain, medulla oblongata, hypothalamus, thalamus, epithalamus, amygdala, superior colliculus, cerebral cortex, neocortex, allocortex, hippocampus, claustrum, olfactory bulb, frontal lobe, temporal lobe, parietal lobe, occipital lobe, caudate-putamen, external globus pallidus, internal globus pallidus, subthalamic nucleus, substantia nigra, thalamus, and motor cortex regions of the brain.

Functional neuroimaging and electrophysiology data may be acquired for any type of neuron including, without limitation, unipolar neurons, bipolar neurons, multipolar neurons, Golgi I neurons, Golgi II neurons, anaxonic neurons, pseudounipolar neurons, interneurons, motor neurons, sensory neurons, afferent neurons, efferent neurons, cholinergic neurons, GABAergic neurons, glutamatergic neurons, dopaminergic neurons, serotonergic neurons, histaminergic neurons, Purkinje cells, spiny projection neurons, Renshaw cells, and granule cells, or a combination thereof.

In certain embodiments, the method further comprises performing optical imaging or multiphoton microscopy of the one or more regions of interest in the brain of the subject.

In certain embodiments, the subject has a neurological disease or disorder.

In certain embodiments, the method further comprises detecting a change in brain function in the subject compared to brain function of a control subject based on said modeling of brain function.

In certain embodiments, the method further comprises identifying a neural circuit involved in pathological changes associated with a neurological disease or disorder.

In certain embodiments, the method further comprises detecting a change in brain function in the subject after administering a treatment for a neurological disease or disorder compared to brain function of the subject before the treatment based on said modeling brain function of the subject before and after administering the treatment.

In certain embodiments, the functional neuroimaging and/or electrophysiology data is acquired while the subject is performing a task or responding to a stimulus. In some embodiments, the method further comprises identifying a neural circuit involved in performing the task or responding to the stimulus. In certain embodiments, the functional neuroimaging data and the experimental electrophysiology data is acquired while the subject is in a resting state (e.g., to allow comparison to data acquired when the subject is performing a task or responding to a stimulus).

In certain embodiments, the DCM is classical DCM, stochastic DCM, spectral DCM, or dynamic DCM.

In another aspect, a computer implemented method for modeling brain function is provided, the computer performing steps comprising: a) receiving functional neuroimaging data and experimental electrophysiology data for one or more brain regions of interest of a subject; b) fitting the functional neuroimaging data to a dynamic causal model; c) calculating neural inter-regional and intra-regional connectivity strength estimates from the dynamic causal model; d) generating a biophysics model that simulates synthetic electrophysiology data from the inter-regional and intra-regional connectivity strength estimates; e) comparing the synthetic electrophysiology data to the experimental electrophysiology data; f) adjusting the biophysical model iteratively until model convergence is reached with the experimental electrophysiology data; and g) displaying information regarding the modeling of brain function.

In certain embodiments, the functional neuroimaging data comprises functional magnetic resonance imaging (fMRI) data, positron emission tomography (PET) data, functional near-infrared spectroscopy (fNIRS) data, single-photon emission computed tomography (SPECT) data, or functional ultrasound imaging (fUS) data.

In certain embodiments, the experimental electrophysiology data comprises electroencephalography (EEG) data, magnetoencephalography (MEG) data, or patch-clamping data.

In certain embodiments, the subject has a neurological disease or disorder, wherein said displaying information comprises listing one or more neural circuits involved in pathological changes associated with the neurological disease or disorder.

In certain embodiments, the functional neuroimaging data and the experimental electrophysiology data are acquired while the subject is performing a task or responding to a stimulus, wherein said displaying information comprises listing one or more neural circuits involved in performing the task or responding to the stimulus. In certain embodiments, the functional neuroimaging data and the experimental electrophysiology data are acquired while the subject is in a resting state (e.g., to allow comparison to data acquired when the subject is performing a task or responding to a stimulus).

In another aspect, a system for modeling brain function using the computer implemented method, described herein, is provided, the system comprising: a) a storage component for storing data, wherein the storage component has instructions for modeling brain function based on analysis of the functional neuroimaging data and experimental electrophysiology data stored therein; b) a computer processor for processing the functional neuroimaging data and experimental electrophysiology data using one or more algorithms, wherein the computer processor is coupled to the storage component and configured to execute the instructions stored in the storage component in order to receive the inputted functional neuroimaging data and experimental electrophysiology data and analyze the data according to the computer implemented method described herein; and c) a display component for displaying the information regarding the modeling of brain function.

In another aspect, a non-transitory computer-readable medium is provided, the non-transitory computer-readable medium comprising program instructions that, when executed by a processor in a computer, causes the processor to perform the computer implemented method described herein.

In another aspect, a kit comprising the non-transitory computer-readable medium and instructions for modeling brain function from functional neuroimaging data and experimental electrophysiology data is provided.

DETAILED DESCRIPTION OF THE INVENTION

Figure 1:
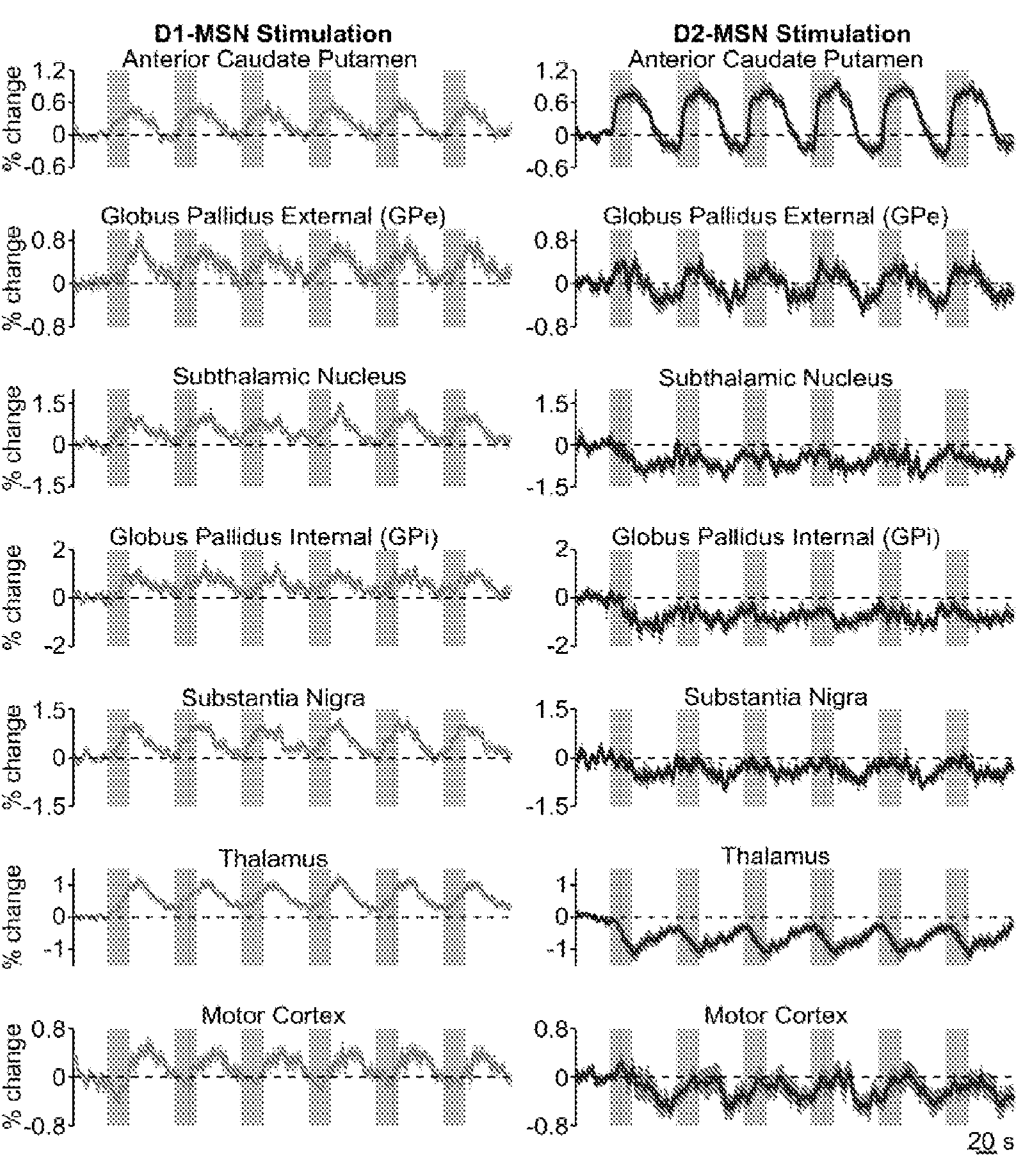
FIG. 1 shows modeling with fMRI BOLD data of 7 regions of interest. The experimental BOLD data was averaged over all subjects. Optical stimulations were at 20 Hz 20 s ON-20 s OFF-20 s ON per cycle, which was repeated 6 times. The regions of interest are the caudate-putamen (CPu), external globus pallidus (GPe), internal globus pallidus (GPi), subthalamic nucleus (STN), substantia nigra (SN), thalamus (THL), motor cortex (MCX).

Methods, systems, and devices, including computer programs encoded on a computer storage medium are provided for combined dynamic causal modeling and biophysics modeling of brain function. In particular, the disclosed methods of modeling brain function can be used to integrate brain function measurements by two or more methods, such as functional magnetic resonance imaging (fMRI) and electrophysiology. Sequential model fitting is used to improve modeling accuracy to generate a more comprehensive model of brain neuronal circuitry.

Before the present compositions, methods, and kits are described, it is to be understood that this invention is not limited to particular methods or compositions described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a neuron" includes a plurality of such neurons and reference to "the measurement" includes reference to one or more measurements and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

The term "about," particularly in reference to a given quantity, is meant to encompass deviations of plus or minus five percent.

The term "connectivity" refers to causal, functional, or directed coupling between brain regions and/or neuronal populations. Neural processing may involve an integrated network of several regions of the brain and functional connectivity of spatially remote brain regions. Analysis of functional connectivity may involve detecting inter-regional and intra-regional neural interactions involved in brain activity during particular cognitive or motor tasks or from spontaneous activity during rest. Neural inter-regional and intra-regional "connectivity strengths" may be estimated from dynamic causal modeling of brain function.

The terms "individual", "subject", "host", and "patient", are used interchangeably herein and refer to any subject with a brain, including invertebrates and vertebrates such as, but not limited to, arthropods (e.g., insects, crustaceans, arachnids), cephalopods (e.g., octopuses, squids), amphibians (e.g., frogs, salamanders, caecilians), fish, reptiles (e.g., turtles, crocodilians, snakes, amphisbaenians, lizards, tuatara), mammals, including human and non-human mammals such as non-human primates, including chimpanzees and other apes and monkey species; laboratory animals such as mice, rats, rabbits, hamsters, guinea pigs, and chinchillas; domestic animals such as dogs and cats; farm animals such as sheep, goats, pigs, horses and cows; and birds such as domestic, wild and game birds, including chickens, turkeys and other gallinaceous birds, ducks, and geese. In some cases, the methods of the invention find use in experimental animals, in veterinary application, and in the development of animal models for disease, including, but not limited to, rodents including mice, rats, and hamsters; primates, and transgenic animals.

It will be apparent to one of ordinary skill in the art that various changes and modifications can be made without departing from the spirit or scope of the invention.

Modeling Brain Function Using Dynamic Causal Modeling in Combination with Biophysics Modeling Methods are provided for using dynamic causal modeling in combination with biophysics modeling to generate improved models of brain function. In particular, the subject methods can be used to integrate brain function measurements by two or more techniques, such as functional neuroimaging and electrophysiology. For example, functional neuroimaging can be performed to image neural activity in one or more regions of interest in a brain of a subject. In addition, electrophysiology measurements may be made on one or more neurons in the same brain regions of interest. First, functional neuroimaging data of brain neural activity is fit to a dynamic causal model (DCM), which is used to calculate neural inter-regional and intra-regional connectivity strength estimates. Next, a biophysics model is constructed using the inter-regional and intra-regional connectivity strength estimates calculated from the DCM analysis. This biophysics model is used to simulate synthetic electrophysiology data, which can be compared to the experimental electrophysiology data that was acquired for the neurons in the brain regions of interest. The biophysical model can be iteratively adjusted until model convergence is reached with the experimental electrophysiology data. In this method, sequential model fitting is used to improve modeling accuracy to generate a more accurate and comprehensive model of brain neuronal circuitry.

The methods described herein are applicable to modeling brain function in any subject having a brain, including invertebrates and vertebrates such as, but not limited to, arthropods (e.g., insects, crustaceans, arachnids), cephalopods (e.g., octopuses, squids), amphibians (e.g., frogs, salamanders, caecilians), fish, reptiles (e.g., turtles, crocodilians, snakes, amphisbaenians, lizards, tuatara), mammals, including human and non-human mammals such as non-human primates, including chimpanzees and other apes and monkey species; laboratory animals such as mice, rats, rabbits, hamsters, guinea pigs, and chinchillas; domestic animals such as dogs and cats; farm animals such as sheep, goats, pigs, horses and cows; and birds such as domestic, wild and game birds, including chickens, turkeys and other gallinaceous birds, ducks, and geese. In some cases, the methods of the invention find use in experimental animals, in veterinary application, and in the development of animal models for disease, including, but not limited to, rodents including mice, rats, and hamsters; primates, and transgenic animals.

Exemplary functional neuroimaging techniques that can be used in the practice of the subject methods include, without limitation, functional magnetic resonance imaging (fMRI), positron emission tomography (PET), functional near-infrared spectroscopy (fNIRS), single-photon emission computed tomography (SPECT), and functional ultrasound imaging (fUS). These functional neuroimaging techniques measure localized changes in cerebral blood flow and changes in the composition of blood related to neural activity. Functional neuroimaging is useful for noninvasively detecting patterns of brain activity associated with specific stimuli or tasks.

In some embodiments, fMRI is used to monitor temporal changes in blood flow associated with changes in levels of brain activity. Blood flow increases upon neuronal activation when a region of the brain is in use. Changes in brain activity can be imaged using fMRI by detection of blood oxygen-level dependent (BOLD) signals. For a description of fMRI and methods of using fMRI for imaging of brain activity, see, e.g., Ogawa, et al. (1990) Magnetic Resonance in Medicine 14 (1):68-78, Kim et al. (2002) Curr Opin Neurobiol. 12(5):607-15, Kim et al. (2012) J Cereb Blood Flow Metab. 32(7):1188-206, Bandettini (2012) Neuroimage 62(2):575-88; Zarghami et al. (2020) Neuroimage 207: 116453; Logothetis, N. K. (Jun. 12, 2008), Logothetis et al. (2008) Nature 453 (7197):869-78, and Logothetis et al. (2001) Nature. 412 (6843):150-157; herein incorporated by reference.

In some embodiments, PET is used to monitor changes in blood flow associated with changes in neural activity. PET uses a radioactive tracer that emits positrons for imaging. Brain activity can be imaged using PET by detection of changes in blood flow, which can be measured indirectly, for example, using an oxygen-15 tracer. Areas having higher levels of radioactivity are associated with increased brain activity. For a description of PET and methods of using PET for imaging of brain activity, see, e.g., Hiura et al. (2014) J Cereb Blood Flow Metab. 34(3):389-96, Baron et al. (2012) Neuroimage 61(2):492-504, Law (2007) Dan Med Bull. 2007 November; 54(4):289-305, Ramsey et al. (1996) J Cereb Blood Flow Metab. 16(5):755-64; herein incorporated by reference.

In some embodiments, SPECT imaging is used in brain imaging. Like PET, SPECT also uses a radioactive tracer for detecting changes in blood flow, but instead uses a tracer that emits gamma rays detectable by a gamma camera. Brain activity can be imaged by detecting changes in blood flow, for example, using Technetium $^{99}$mTc-exametazime or $^{99}$mTc-D,L-hexamethylene-propyleneamine oxime. For a description of SPECT and methods of using SPECT for imaging of brain activity, see, e.g., Cuocolo et al. (2018) Int Rev Neurobiol 141:77-96, Andersen (1989) Cerebrovasc Brain Metab Rev. 1(4):288-318, Matsuda (2001) Ann Nucl Med 15(2):85-92, Gonul et al. (2009) Int Rev Psychiatry 21(4):323-35; herein incorporated by reference.

In some embodiments, fNIRS is used to monitor changes in the composition of blood near a neural event. In particular, fNIRS can be used to detect changes in levels of oxyhemoglobin and deoxyhemoglobin using near-infrared light. Based on differences in the absorption spectra of oxyhemoglobin and deoxyhemoglobin, relative changes in hemoglobin concentration can be measured with fNIRS. Cerebral hemodynamic responses correlate with cerebral activation or deactivation. For a description of fNIRS and methods of using fNIRS for imaging of brain activity, see, e.g., Tachtsidis et al. (2020) Ann N Y Acad Sci. 1464(1):5-29, Ferrari et al. (2012) Neuroimage 63(2):921-35, Scholkmann et al. (2014) Neuroimage 85 Pt 1:6-27, Kim et al. (2017) Mol Cells 40(8):523-532; herein incorporated by reference.

In some embodiments, fUS is used to monitor localized changes in cerebral blood volume that correlate with changes in neural activity. For a description of fUS and methods of using fUS for imaging of brain activity, see, e.g., Bleton et al. (2016) BMC Med Imaging 12; 16:22, Raaij et al. (2012) Neuroimage 63(3):1030-7; herein incorporated by reference.

Electrophysiology techniques are used to measure electrical properties in the brain, typically voltage or current changes of neurons. Exemplary electrophysiology techniques that can be used in the practice of the subject methods include, without limitation, electroencephalography (EEG), magnetoencephalography (MEG), and patch-clamping. These electrophysiology techniques are useful for identifying the specific types of neurons involved in neural networks and measuring neuron-specific changes in activity associated with brain responses.

In some embodiments, EEG is used to record neuronal electrical activity in the brain. EEG can be performed noninvasively with electrodes placed on the scalp. EEG measurements have the advantage of having high temporal resolution and can detect changes in electrical activity in the brain on a millisecond time scale. For a description of EEG and methods of using EEG for recording electrical activity in the brain, see, e.g., Niedermeyer et al. (2004) Electroencephalography: Basic Principles, Clinical Applications, and Related Fields. Lippincott Williams & Wilkins; Jackson et al. (2014) Psychophysiology 51(11):1061-71, Khanna et al. (2015) Neurosci Biobehav Rev. 49:105-13, Feyissa et al. (2019) Handb Clin Neurol. 160:103-124, Beres et al. (2017) Appl Psychophysiol Biofeedback 42(4):247-255; herein incorporated by reference.

In some embodiments, MEG is used to record magnetic fields produced by electrical currents generated in the brain. MEG detects weak magnetic fields produced by synchronized neuronal currents (i.e., ionic currents flowing in the dendrites of neurons during synaptic transmission). These weak magnetic fields can be detected using a magnetometer such as a superconducting quantum unit interference device (SQUID) or a spin exchange relaxation-free (SERF) magnetometer. For a description of MEG and methods of using MEG for recording magnetic fields associated with neuronal activity in the brain, see, e.g., Hamalainen et al. (1993) Reviews of Modern Physics. 65 (2):413-497, Baillet et al. (2017) Nat Neurosci. 20(3):327-339, Gross et al. (2019) Neuron 104(2):189-204, Stapleton-Kotloski et al. (2018) Brain Sci. 8(8):157; herein incorporated by reference.

Dynamic causal modeling (DCM) is a Bayesian generative modeling paradigm that can model the causal relations in the brain taking into account neuronal dynamics, modulatory inputs, and observational data (e.g., BOLD fMRI, EEG, or MEG). DCM can be used to estimate coupling among brain regions and quantify effective connectivity strengths among neuronal populations in one or more regions of the brain. A dynamic causal model of interacting neural populations can be used to estimate neural inter-regional and intra-regional connectivity strengths from functional neuroimaging data using Bayesian statistical methods. The model may include interactions between excitatory and inhibitory neural populations. Different types of DCM can be used in calculating the connectivity strength estimates. Classical DCM assumes no state noise whereas stochastic DCM (sDCM) utilizes state noise to account for uncertainty due to neighboring regions. Spectral DCM is another paradigm that assumes state noise, but in this approach, model fitting is performed over the cross spectra of the system, which makes sDCM useful for resting state modeling. Dynamic effective connectivity (or dynamic DCM) is another approach that is useful for investigating temporal changes in connectivity strengths. For a description of different types of DCM approaches, see, e.g., Friston et al. (2003) Neuroimage 19(4):1273-1302, Friston et al. (2014) NeuroImage 94:396-407, Park et al. (2018) Neuroimage 180:594-608, Li et al. (2011) NeuroImage 58(2):442-457, Stephan et al. (2010) NeuroImage 49 (4):3099-3109, Stephan et al. (2008) NeuroImage. 42 (2):649-662, Marreiros et al. NeuroImage 39 (1):269-278, Razi et al. (2015) NeuroImage 106:1-14, and Lee et al. (2006) NeuroImage. 30 (4):1243-1254; herein incorporated by reference.

Biophysics modeling is based on the biophysics attributes of neurons and brain regions. A biophysics neuronal model may include various biophysics attributes including, but not limited to, firing patterns of individual neurons, neuronal types, receptors, inputs and outputs, topological structures, and self-connectivity. The present method utilizes a biophysics model to simulate synthetic electrophysiology data using the inter-regional and intra-regional connectivity strength estimates from dynamic causal modeling. Next, the synthetic electrophysiology data is compared to the experimental electrophysiology data acquired from the subject, and the model is improved by adjusting it iteratively to reach convergence. For a description of biophysics modeling, see, e.g., Example 5, Hill and Tononi (2005) Journal of Neurophysiology 93(3):1671-1698, and Murray et al. (2018) Biol Psychiatry Cogn Neurosci Neuroimaging 3(9):777-787; herein incorporated by reference.

In some embodiments, functional neuroimaging and electrophysiology techniques are used in combination to detect brain responses when a subject is exposed to stimuli or performing tasks. Additionally, functional neuroimaging and electrophysiology measurements of brain activity can be taken while the subject is in a resting state (e.g., absence of stimulus or taskless) to allow brain activity to be compared to a subject's "baseline" brain state, i.e., to identify brain regions exhibiting changes in neural activity associated with specific stimuli or tasks.

In some embodiments, the methods described herein are used to evaluate changes in brain function in response to optogenetic perturbation of neural activity. In certain embodiments, optogenetics is used to induce cell-specific perturbations in the brain. For example, optogenetics can be used to excite or inhibit one or more selected neurons of interest using light. For a description of optogenetics techniques, see, e.g., Abe et al., 2012; Desai et al., 2011; Duffy et al., 2015; Gerits et al., 2012; Kahn et al., 2013; Lee et al., 2010; Liu et al., 2015; Ohayon et al., 2013; Weitz et al., 2015; Weitz and Lee, 2013; herein incorporated by reference.

The methods described herein can also be used to evaluate changes in brain function in response to brain stimulation with electrical currents or magnetic fields that are applied to a selected brain area. For example, electrical brain stimulation (EBS) can be used to stimulate a neuron or neural network in the brain through the direct or indirect excitation of its cell membrane by using an electric current. For a description of EBS techniques, see, e.g., Aum et al. (2018) Front Biosci (Landmark Ed) 23:162-182, Tellez-Zenteno et al. (2011) Neurosurg Clin N Am. 22(4):465-75, Padberg et al. (2009) Exp. Neurol. 219:2-13, Nahas et al. (2010) Biol. Psychiatry 67:101-109, Lefaucheur et al. (2010) Exp. Neurol. 223:609-614, Levy et al. (2008) J. Neurosurg. 108:707-714, Hanajima et al. (2002) Clin. Neurophysiol. 113:635-641, Picillo et al. (2015) Brain Stimul. 8:840-842, Canavero (2014) Textbook of Cortical Brain Stimulation. Berlin: De Gruyter Open; herein incorporated by reference. Alternatively, transcranial magnetic stimulation (TMS) can be used to electrically stimulate the brain by electromagnetic induction and can be used to noninvasively stimulate specific regions of the brain. For a description of TMS techniques, see, e.g., Klomjai et al. (2015) Ann Phys Rehabil Med. 58(4):208-213, Lefaucheur (2019) Handb Clin Neurol. 160: 559-580, Burke et al. (2019) Handb Clin Neurol. 163:73-92; herein incorporated by reference.

In some embodiments, the methods described herein are used to evaluate changes in brain activity in response to a subject performing cognitive or motor tasks. Such tasks may include, for example, without limitation, tests of memory, intelligence, speech/language, emotion, executive function (e.g., problem solving, planning, organizational skills, selective attention, inhibitory control), visuospatial function, balance, or physical activity/exercise (e.g., walking, running, limb movement). The methods described herein can be used to analyze the intra-regional and inter-regional neural interactions involved in brain activity during particular cognitive or motor tasks and compared to brain activity of the subject in a resting state.

Brain function may be modeled by the present methods for any region or regions of the brain. In certain embodiments, the one or more brain regions of interest are in the cerebrum, cerebellum, or brainstem regions of the brain. Brain regions of interest may include, without limitation, the basal ganglia, striatum, medulla, pons, midbrain, medulla oblongata, hypothalamus, thalamus, epithalamus, amygdala, superior colliculus, cerebral cortex, neocortex, allocortex, hippocampus, claustrum, olfactory bulb, frontal lobe, temporal lobe, parietal lobe, occipital lobe, caudate-putamen, external globus pallidus, internal globus pallidus, subthalamic nucleus, substantia nigra, thalamus, and motor cortex regions of the brain.

Functional neuroimaging and electrophysiology data may be acquired for any type of neuron including, without limitation, unipolar neurons, bipolar neurons, multipolar neurons, Golgi I neurons, Golgi II neurons, anaxonic neurons, pseudounipolar neurons, interneurons, motor neurons, sensory neurons, afferent neurons, efferent neurons, cholinergic neurons, GABAergic neurons, glutamatergic neurons, dopaminergic neurons, serotonergic neurons, histaminergic neurons, Purkinje cells, spiny projection neurons, Renshaw cells, and granule cells, or a combination thereof.

System and Computer Implemented Methods for Modeling Brain Function

In a further aspect, the invention includes a computer implemented method for modeling brain function using a combination of dynamic causal modeling and biophysics modeling, as described herein. The computer performs steps comprising a) receiving functional neuroimaging data and experimental electrophysiology data for one or more brain regions of interest of a subject; b) fitting the functional neuroimaging data to a dynamic causal model; c) calculating neural inter-regional and intra-regional connectivity strength estimates from the dynamic causal model; d) generating a biophysics model that simulates synthetic electrophysiology data from the inter-regional and intra-regional connectivity strength estimates; e) comparing the synthetic electrophysiology data to the experimental electrophysiology data; f) adjusting the biophysical model iteratively until model convergence is reached with the experimental electrophysiology data; and g) displaying information regarding the modeling of brain function.

In certain embodiments, the functional neuroimaging data comprises functional magnetic resonance imaging (fMRI) data, positron emission tomography (PET) data, functional near-infrared spectroscopy (fNIRS) data, single-photon emission computed tomography (SPECT) data, or functional ultrasound imaging (fUS) data.

In certain embodiments, the experimental electrophysiology data comprises electroencephalography (EEG) data, magnetoencephalography (MEG) data, or patch-clamping data.

The method can be implemented in digital electronic circuitry, or in computer software, firmware, or hardware. The disclosed and other embodiments can be implemented as one or more computer program products, i.e., one or more modules of computer program instructions encoded on a computer readable medium for execution by, or to control the operation of, a data processing apparatus. The computer readable medium can be a machine-readable storage device, a machine-readable storage substrate, a memory device, a composition of matter effecting a machine-readable propagated signal, or any combination thereof.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

In a further aspect, a system for performing the computer implemented method, as described, is provided. Such a system includes a computer containing a processor, a storage component (i.e., memory), a display component, and other components typically present in general purpose computers. The storage component stores information accessible by the processor, including instructions that may be executed by the processor and data that may be retrieved, manipulated or stored by the processor.

The storage component includes instructions. For example, the storage component includes instructions for modeling brain function based on analysis of functional neuroimaging data and experimental electrophysiology data stored therein. The computer processor is coupled to the storage component and configured to execute the instructions stored in the storage component in order to receive the functional neuroimaging data and experimental electrophysiology data and analyze the data according to one or more algorithms using dynamic causal modeling and biophysics modeling, as described herein. The display component displays information regarding the modeling of brain function. In certain embodiments, the functional neuroimaging data and experimental electrophysiology data is acquired from a subject who has a neurological disease or disorder, wherein the information displayed regarding the modeling of brain function comprises listing one or more neural circuits involved in pathological changes associated with the neurological disease or disorder. In certain embodiments, the functional neuroimaging data and the experimental electrophysiology data is acquired while the subject is performing a task or responding to a stimulus, wherein the information displayed regarding the modeling of brain function comprises listing one or more neural circuits involved in performing the task or responding to the stimulus. In certain embodiments, the functional neuroimaging data and the experimental electrophysiology data is acquired while the subject is in a resting state (e.g., to allow comparison to data acquired when the subject is performing a task or responding to a stimulus).

The storage component may be of any type capable of storing information accessible by the processor, such as a hard-drive, memory card, ROM, RAM, DVD, CD-ROM, USB Flash drive, write-capable, and read-only memories. The processor may be any well-known processor, such as processors from Intel Corporation. Alternatively, the processor may be a dedicated controller such as an ASIC.

The instructions may be any set of instructions to be executed directly (such as machine code) or indirectly (such as scripts) by the processor. In that regard, the terms "instructions," "steps" and "programs" may be used interchangeably herein. The instructions may be stored in object code form for direct processing by the processor, or in any other computer language including scripts or collections of independent source code modules that are interpreted on demand or compiled in advance.

Data may be retrieved, stored or modified by the processor in accordance with the instructions. For instance, although the system is not limited by any particular data structure, the data may be stored in computer registers, in a relational database as a table having a plurality of different fields and records, XML documents, or flat files. The data may also be formatted in any computer-readable format such as, but not limited to, binary values, ASCII or Unicode. Moreover, the data may comprise any information sufficient to identify the relevant information, such as numbers, descriptive text, proprietary codes, pointers, references to data stored in other memories (including other network locations) or information which is used by a function to calculate the relevant data.

In certain embodiments, the processor and storage component may comprise multiple processors and storage components that may or may not be stored within the same physical housing. For example, some of the instructions and data may be stored on removable CD-ROM and others within a read-only computer chip. Some or all of the instructions and data may be stored in a location physically remote from, yet still accessible by, the processor. Similarly, the processor may comprise a collection of processors which may or may not operate in parallel.

Kits

Kits are also provided for carrying out the methods of modeling brain function from functional neuroimaging data and experimental electrophysiology data using a combination of dynamic causal modeling and biophysics modeling, as described herein. In some embodiments, the kit comprises software for carrying out the computer implemented methods for modeling brain function using a combination of dynamic causal modeling and biophysics modeling. In some embodiments, the kit comprises a system for modeling brain function, as described herein.

In addition, the kits may further include (in certain embodiments) instructions for practicing the subject methods. These instructions may be present in the subject kits in a variety of forms, one or more of which may be present in the kit. For example, instructions may be present as printed information on a suitable medium or substrate, e.g., a piece or pieces of paper on which the information is printed, in the packaging of the kit, in a package insert, and the like. Another form of these instructions is a computer readable medium, e.g., diskette, compact disk (CD), flash drive, and the like, on which the information has been recorded. Yet another form of these instructions that may be present is a website address which may be used via the internet to access the information at a removed site.

Utility

The disclosed methods will find many uses in research and development in the neuroscience field, particularly in the study of brain function and dysfunction as well as the development of therapeutics for treatment of neurological diseases and disorders. The modeling approach combining DCM and biophysics modeling, described herein, can relate different types of data having different spatial and temporal resolutions. In particular, the inventors have demonstrated that using DCM and biophysics modeling in combination can generate a more comprehensive brain function model that reproduces both fMRI and electrophysiology data (See Examples). Thus, this modeling approach is useful for interpretation of experimental data obtained by different techniques and for testing neuroscience hypotheses. Applications of this modeling approach include basic research into neurological processes involved in cognitive and motor function, identifying neural circuits and determining their function in various regions of the brain, identifying neural circuits and brain regions affected by pathology in subjects with neurological diseases and disorders, and monitoring brain responses to therapeutics for treating neurological diseases and disorders.

The subject methods are applicable to modeling of brain function for any region of the brain, including, without limitation, the cerebrum or regions thereof including, but not limited to, the frontal lobe, parietal lobe, temporal lobe, or occipital lobe, gyri (e.g., frontal gyrus, temporal gyrus, precentral gyrus, postcentral gyrus, or cingulate gyrus), sulci (e.g., central sulcus, cingulate sulcus, calcarine sulcus, callosal sulcus, or hippocampal sulcus), cerebral cortex (e.g., neocortex or allocortex), and corpus callosum; cerebellum or regions thereof including, but not limited to, the anterior lobe, posterior lobe, and flocculonodular lobe; the brainstem or regions thereof including, but not limited to, the midbrain, pons and medulla; or the basal ganglia or regions thereof including, but not limited to, the striatum, including the dorsal striatum (caudate nucleus and putamen) and the ventral striatum (nucleus accumbens and olfactory tubercle), the globus pallidus, the ventral pallidum, the substantia nigra, and the subthalamic nucleus.

The subject methods are also applicable to modeling the function of any type of neuron in any region of the brain or nervous system including, without limitation, unipolar neurons, bipolar neurons, multipolar neurons, Golgi I neurons, Golgi II neurons, anaxonic neurons, pseudounipolar neurons, interneurons (e.g., Basket cells, Lugaro cells, unipolar brush cells, spindle cells), pyramidal neurons (e.g., RSad neurons, RSna neurons, IB neurons, and Betz cells), motor neurons (upper and lower motor neurons), sensory neurons, afferent neurons, efferent neurons, cholinergic neurons, GABAergic neurons, glutamatergic neurons, dopaminergic neurons, serotonergic neurons, histaminergic neurons, cerebellar Purkinje cells, striatum neurons (e.g., spiny projection neurons, cholinergic interneurons, and GABAergic interneurons), Renshaw cells, and granule cells, as well as modeling the function of groups of connected neurons forming neural circuits and inter- and intra-regional connectivity among neurons in one or more selected regions of the brain.

The subject methods are also applicable to modeling of changes in brain function associated with neurological diseases and disorders including, without limitation, brain damage such as, but not limited to, frontal lobe damage, parietal lobe damage, temporal lobe damage, and occipital lobe damage; brain dysfunction such as, but not limited to, aphasia, dysgraphia, dysarthria, apraxia, agnosia, and amnesia; cranial nerve disorders such as, but not limited to, trigeminal neuralgia and hemifacial spasms; autonomic nervous system disorders such as, but not limited to, dysautonomia and multiple system atrophy; seizure disorders such as epilepsy; movement disorders of the central and peripheral nervous system such as, but not limited to, Parkinson's disease, essential tremor, amyotrophic lateral sclerosis, Tourette's syndrome, and multiple sclerosis and various types of peripheral neuropathy; sleep disorders such as narcolepsy; and other neurological diseases and disorders associated with nervous system injury, underdevelopment, biochemical, anatomical, or electrical malfunction, and/or disease pathology such as, but not limited to, attention deficit hyperactivity disorder, autism, Asperger syndrome, obsessive compulsive disorder, Huntington's disease, Alzheimer's disease, multiple sclerosis, and organic psychosis. Additionally, the subject methods can be used for screening therapeutics for treatment of such neurological diseases and disorders as well as monitoring efficacy of a selected treatment.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventors to comprise preferred modes for the practice of the invention. It will be appreciated by those of skill in the art that, in light of the present disclosure, numerous modifications and changes can be made in the particular embodiments exemplified without departing from the intended scope of the invention. All such modifications are intended to be included within the scope of the appended claims.

Example 1

Joint Dynamic Causal Modeling and Biophysics Modeling to Enable Multi-Scale Brain Network Function Modeling We designed a new modeling approach to integrate brain function measurements from different modalities. Brain functions are studied using many different experimental technologies with different spatio-temporal sampling rates and contrast. Some of the modalities utilized include functional magnetic resonance imaging (fMRI), electrophysiology, and optical imaging. Because different technologies offer unique advantages in terms of its ability to probe brain function at different scales while none of them provide a full picture, it is critical to have an approach that enables us to understand how the different measurements can be utilized to construct a comprehensive model of brain function.

In order to construct a comprehensive model of brain function, we needed a strategy to model data from multi-modal imaging/recording. Here, we provide a novel approach that enables comprehensive modeling of whole brain scale function combined with the ability to model spiking level activity. We first fit a model to data from one imaging/recording modality, for example, functional magnetic resonance imaging. Results from this process can, for example, be the connectivity estimates among regions of selection. We then use the outcomes from the model fitting procedure to start modeling of neural activity at the single unit scale. This modeling utilizes findings from the first dataset as a basis and is fitted under their influence. Using this influence from another paradigm for trying to fit the experimental data, we obtain a strong model.

To be more concrete, we provide an example, which can be generalized to other measurement modalities and computational modeling approaches. We used a DCM (Dynamic Causal Model) on fMRI data and a biophysics model on electrophysiology data in the following steps. DCM constituted the first model which influenced the second one, i.e. the biophysical model. The steps of our method are provided below:

1. The fMRI data were fit to a DCM model and the effective inter- and intra-regional connectivity strength estimates were extracted.
2. Using these DCM estimates, we constructed a biophysics model and simulated synthetic electrophysiology data. One may include other biophysics attributes as a hypothesis for testing, such as neuronal types, receptors, inputs and outputs topological structures, etc.
3. Synthetic electrophysiology data was compared with the experimental electrophysiology data. If they match, we concluded our pipeline. If not, we updated the biophysical model and repeated until convergence.

DCM is more of a data-driven approach, while biophysics modeling relies heavily on hypothesis. This joint modeling approach integrates the advantages of DCM and biophysics modeling of their own and compensates for the main drawbacks of each. Using DCM estimates in biophysics modeling also reduced the parameter search time. This biophysics modeling approach in principle has the power to reproduce and interpret fMRI and electrophysiology data, but the parameter space increases exponentially with the number of regions. Biophysics modeling, on the other hand, expands DCM with many physiology details. For example, instead of modeling one brain region as a single node, biophysics modeling describes one region as a group of neurons with inputs and output mechanisms and topological structures.

In summary, by joining the two modeling approaches, we can directly base our analysis on both fMRI and electrophysiology data, and test hypotheses for mechanisms underlying brain functions of interest.

Example 2

Modeling Basal Ganglia in Mice Brains

We used the basal ganglia in mice brains as an example to show that the modeling approach described in Example 1 is a powerful tool to construct a comprehensive model of brain function. Here, we utilized real fMRI and electrophysiology data. Details of dynamic causal modeling (DCM) modeling with optogenetic fMRI (ofMRI) data are described by Bernal-Casas et al. (Neuron, 93(3):522-532, 2017; herein incorporated by reference in its entirety), but for illustration purposes, here we provide a brief description.

Figure 2:
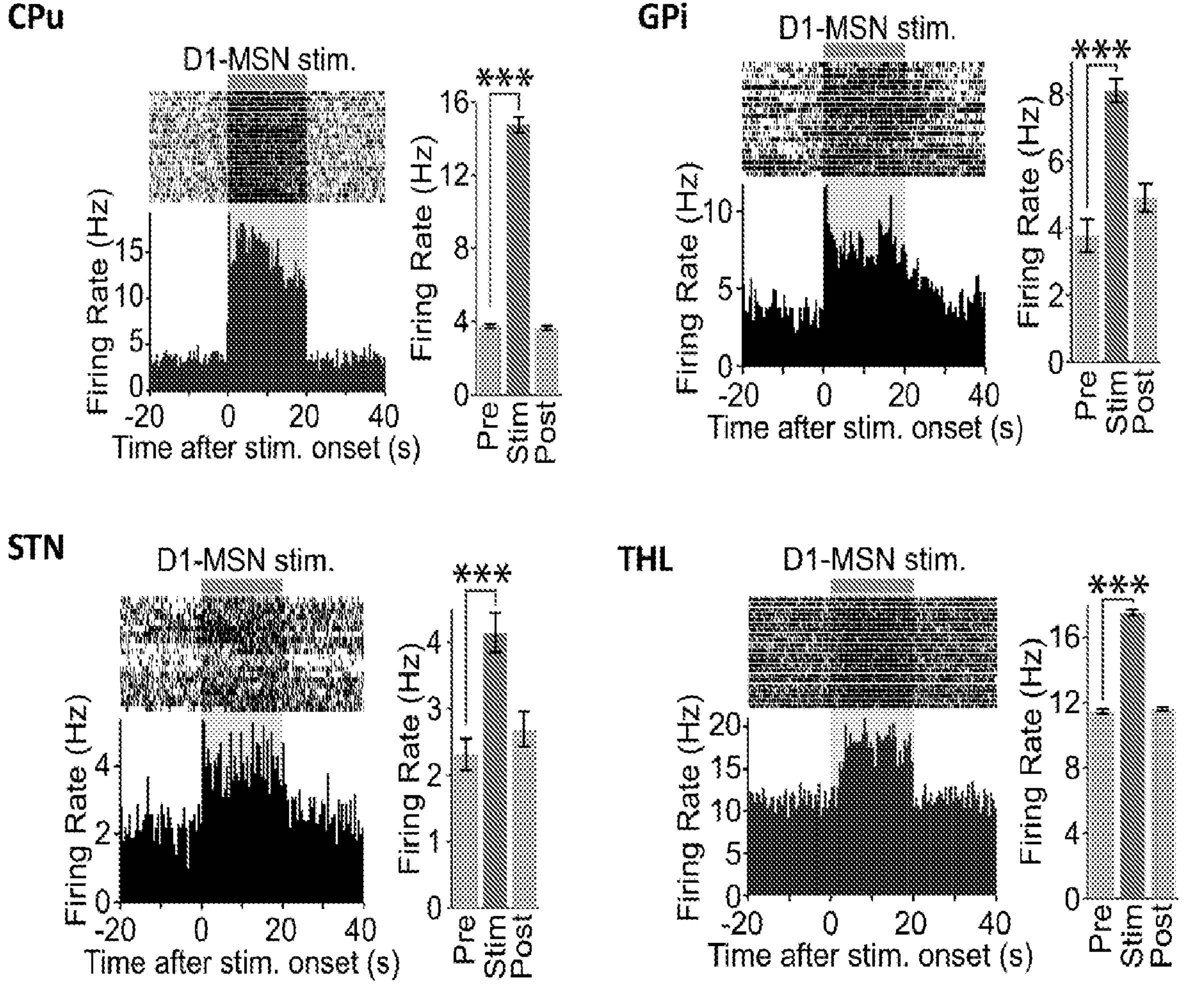
FIG. 2 shows modeling with electrophysiology data of 4 regions of interest.

The basal ganglia is an essential region for motor control and many other important brain functions. This region has been difficult to study due to its anatomically intermingled different types of cells and complicated circuitries. Bernal-Casas et al. (supra) used optogenetic fMRI method to stimulate the D1 and D2 medium spiny neurons in striatum separately, thus gained high-resolution data regarding the pathways associated with the two types of cells in basal ganglia. We performed modeling with fMRI BOLD data of 7 regions of interest and electrophysiology data of 4 regions of interest (FIG. 1 and FIG. 2). FIG. 1 shows experimental BOLD data averaged over all subjects. Optical stimulations were on 20 Hz 20 s ON-20 s OFF-20 s ON cycle and repeated 6 times. Regions of interest are the caudate-putamen (CPu), external globus pallidus (GPe), internal globus pallidus (GPi), subthalamic nucleus (STN), substantia nigra (SN), thalamus (THL), motor cortex (MCX).

Figure 3:
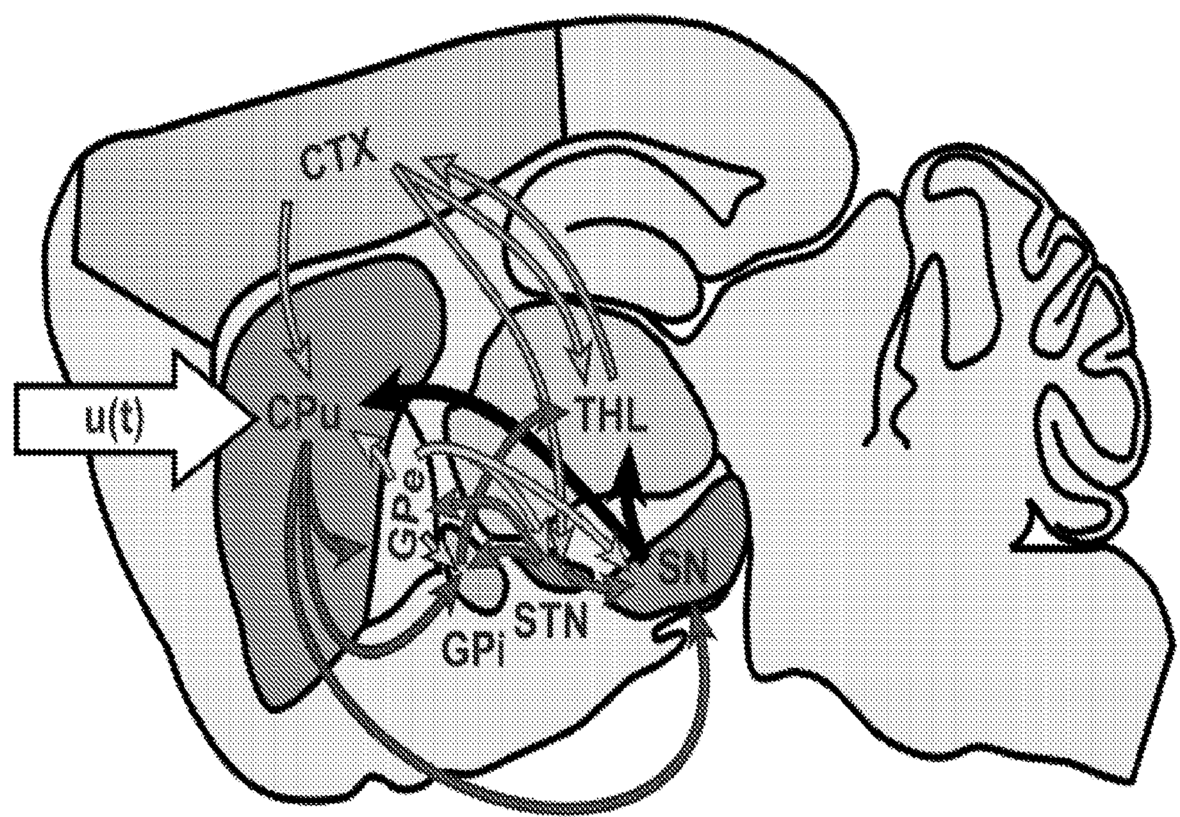
FIG. 3 shows an a priori generative network model. Using the corresponding data for each subject, we first performed a DCM analysis in order to reveal effective connectivity estimates between and within each region using the a priori generative network model.
Figure 4:
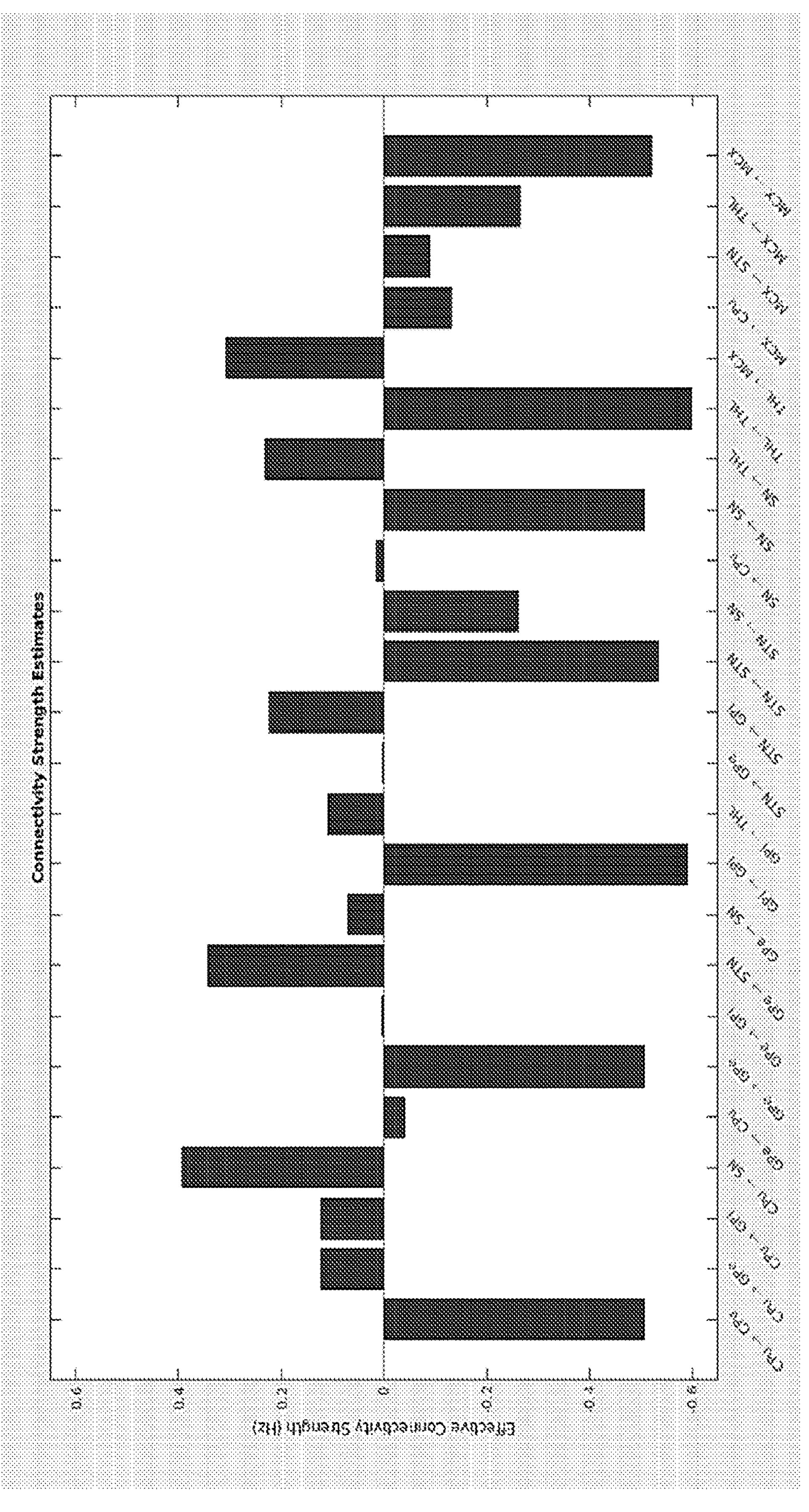
FIG. 4 shows analysis results. Connectivity strength estimates are given in Hz. Magnitudes of parameters in this figure reflect the influence of neuronal activity in a region on the rate of change of neuronal activity in another one. These estimates are then used as an influence on the neuronal population design in biophysical modeling.
Figure 5A:
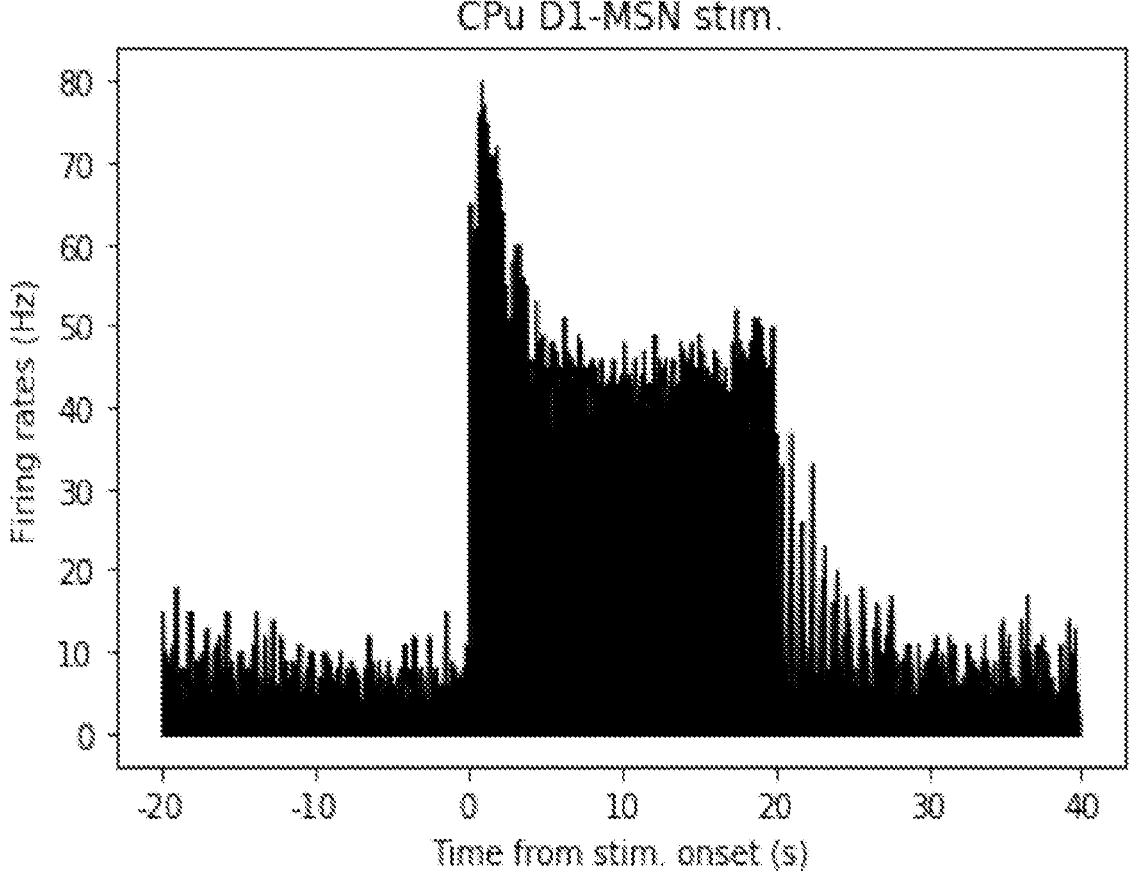
FIGS. 5A-5D show simulated electrophysiology data using a biophysics model. In building the biophysics model, we used the same structural model of mice basal ganglia-thalamocortical loop as in our DCM analysis and a neuronal model modified (Hill and Tononi Journal of neurophysiology, 93(3):1671-1698, 2005; herein incorporated by reference). While in DCM analysis one node represents one region of interest, in the biophysics model, we used 100 neuronal units for one region of interest to better study neuronal level mechanisms. The biophysics model is built without making any hypothesis, i.e., we directly derive the model from connectivity parameters of DCM results.
Figure 5B:
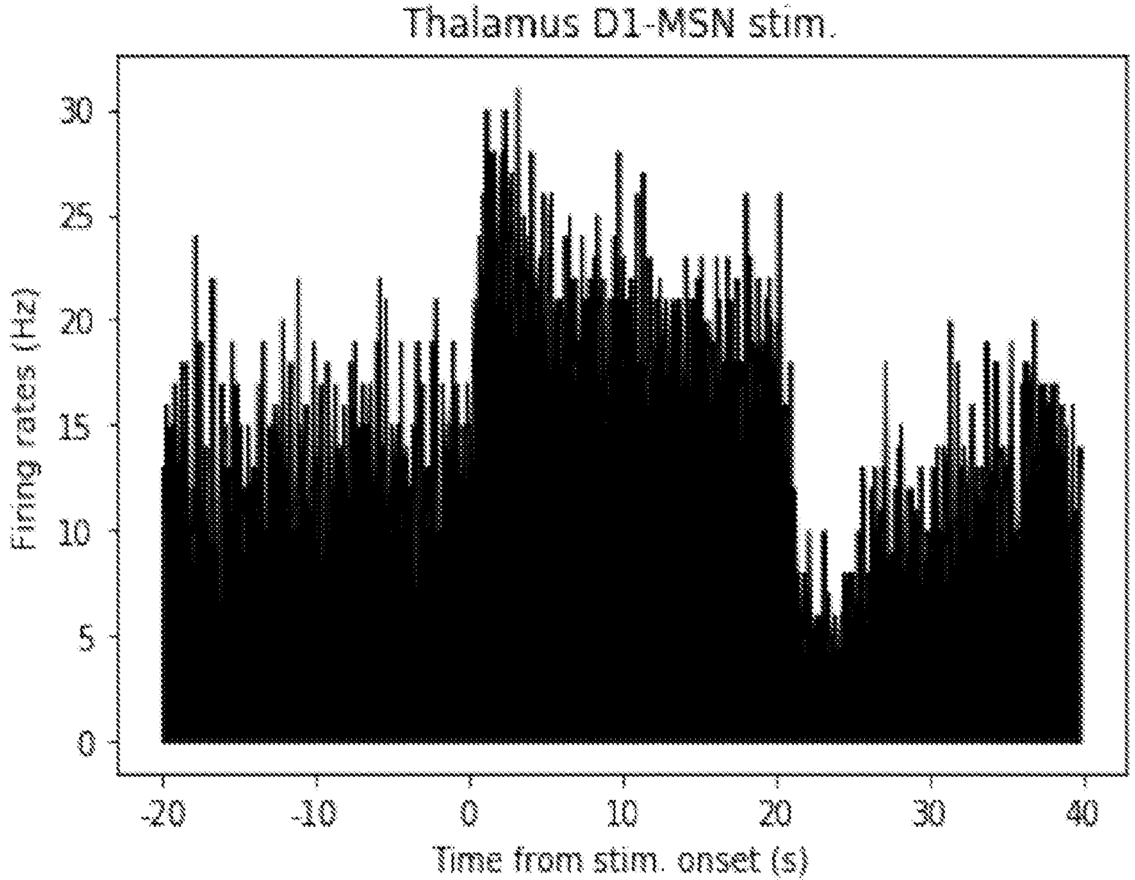
Figure 5C:
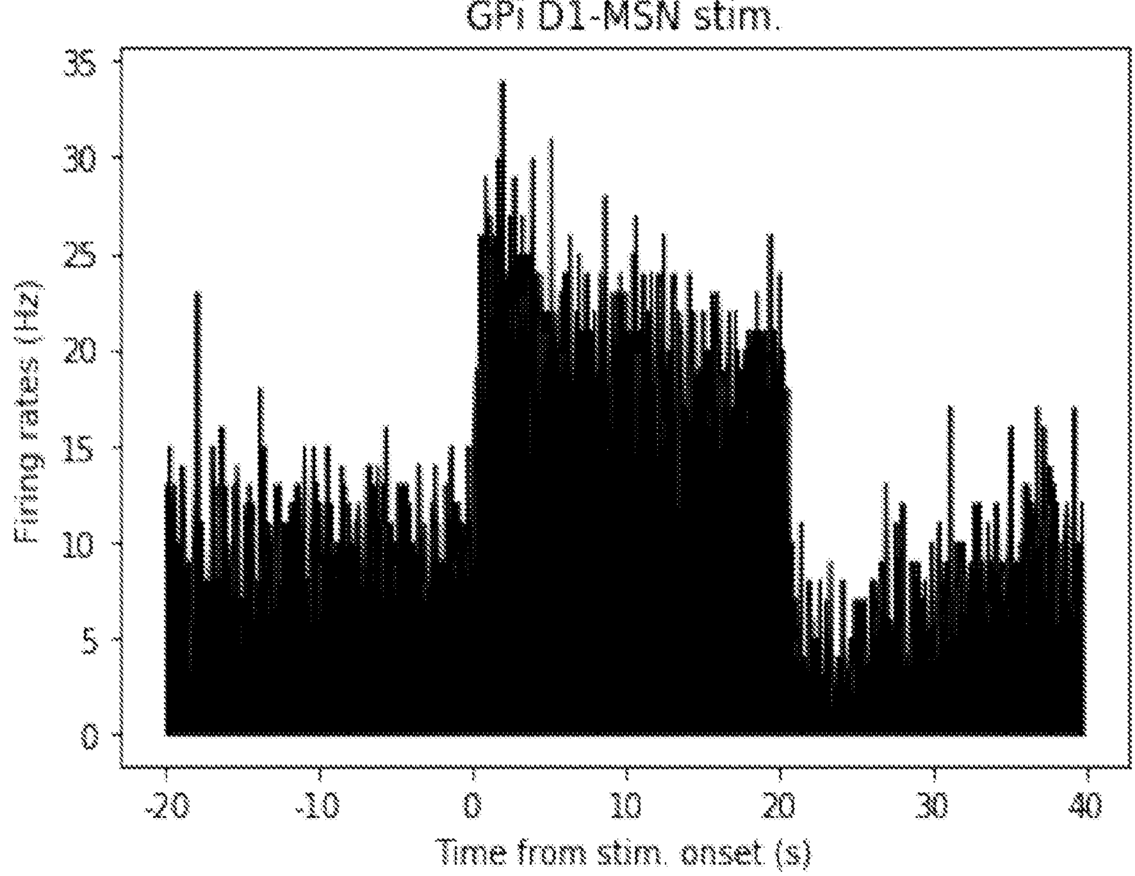
Figure 5D:
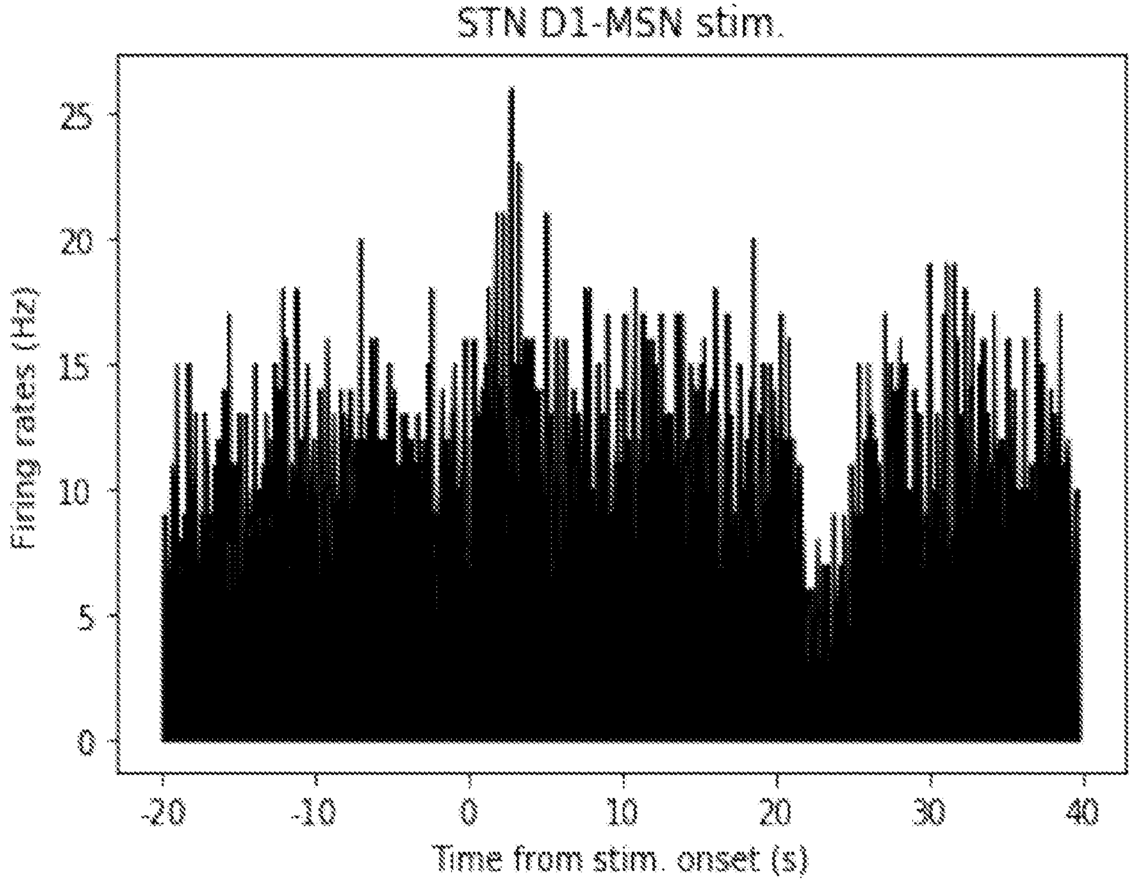

Using the corresponding data for each subject we first performed a DCM analysis in order to reveal effective connectivity estimates between and within each region. For this analysis we employed the a priori generative network model shown in FIG. 3. Analysis results can be found in FIG. 4 where connectivity strength estimates are given in Hz. Magnitudes of the parameters in this figure reflect the influence of neuronal activity in a region on the rate of change of neuronal activity in another one. These estimates are then used as an influence on the neuronal population design in the biophysical modeling.

In building the biophysics model, we used the same structural model of mice basal ganglia-thalamocortical loop as in the DCM analysis and the neuronal model modified from [10]. The Hill and Tononi neuronal model is a type of Hodgkin-Huxley model that features biologically accurate details. While in DCM analysis one node represents one region of interest, in the biophysics model we used 100 neuronal units for one region of interest to better study neuronal level mechanisms. The number of units is set arbitrarily.

We first built a biophysics model without making any hypothesis, i.e., we directly derived the model from connectivity parameters of the DCM results. FIG. 5 shows the simulated electrophysiology data using this model, which agreed with the experimental data shown in FIG. 2. However, DCM is a regional level analysis that may not reflect the true neuronal level mechanisms, so testing a hypothesis of neuronal level mechanisms is the crucial advantage of our biophysics modeling. For example, anatomically the projections from GPi to thalamus are GABAergic which is a type of inhibitory connection. In principle, this connection should lead to opposite polarities of GPi and thalamus activity, but our experiments discovered they both showed increased activity during D1-MSN stimulations.

We hypothesized that the thalamus can be activated in between GPi inhibitory signals, and the synchrony among GPi neurons is the key to this seemingly paradoxical phenomenon. This hypothesis is made based on the observation that the synchrony levels increased among neurons in multiple regions of interest in our D1-MSN stimulation experiments. One thalamus neuron may receive inputs from multiple GPi neurons. Before D1 stimulation occurs, the synchrony level among GPi neurons is relatively low so that one thalamus neuron receives unsynchronized inhibitory inputs from the intrinsic firings of the GPi. During the stimulation, the GPi firings and the inhibitions to the thalamus become more synchronized; thus, intrinsically active thalamus neuron firings can occur in between synchronized GPi inhibitory signals.

Figure 6:
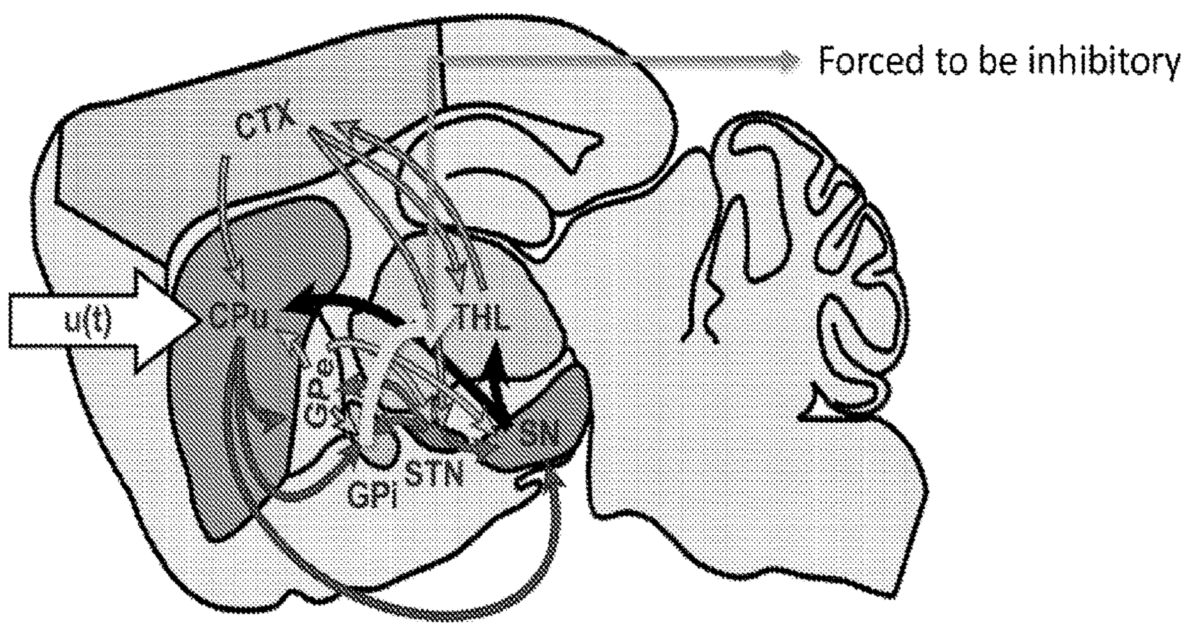
FIG. 6 shows simulated activity in the thalamus.
Figure 6:
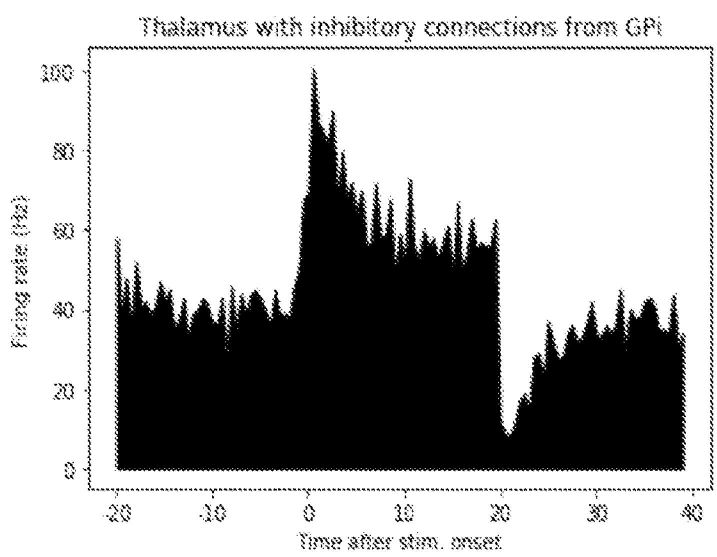
Figure 7:
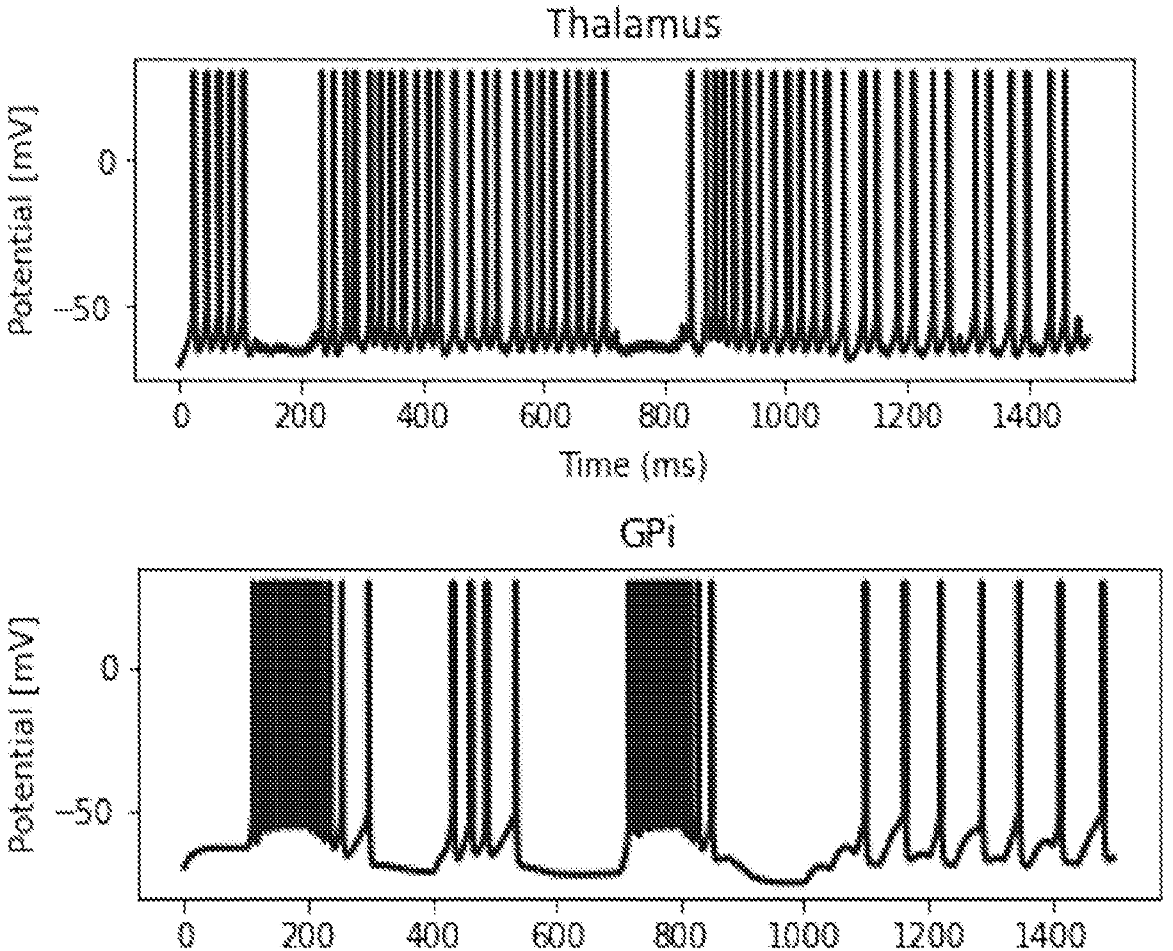
FIG. 7 shows illustrates how one thalamus neuron fires in between GPi inhibitory inputs.

To test this hypothesis, we generated a new model by forcing the connection from GPi to thalamus to be inhibitory. The rest of the model remains the same with the first model. We successfully increased thalamus activity during stimulation in spite of GPi inhibition. FIG. 6 shows the simulated activity in thalamus, and FIG. 7 illustrates how one thalamus neuron fires in between GPi inhibitory inputs. The results demonstrate that our joint DCM and biophysics modeling approach can serve as a powerful tool in explaining both fMRI and electrophysiology data and testing hypotheses of underlying mechanisms.

Example 3

Sequential Model Fitting

Our method can be applied to perform sequential model fitting using the information from one model to improve another when data from more than two different modalities are acquired at different scales. Therefore, all the existing applications of the modeling paradigms that we use can benefit from our method. This makes the number of possible applications large, and they include but are not limited to the following scenarios:

1. Optogenetic experiments in which the selective excitation of cells can be performed during fMRI scan and electrophysiology data acquisition. Our approach will enable comprehensive modeling of brain circuitry.
2. Resting state experiments where there are no direct external inputs to the brain. Collection of resting state fMRI (rsfMRI) and electrophysiology data is common and often followed by connectivity modeling. Our approach will enable comprehensive modeling of brain circuitry.

The experimental methods mentioned above can be used in research on diseases including Parkinson's disease and epilepsy. To exemplify, in [2], MRI and DCM are used to investigate a neural circuit that plays an important role in Parkinson's disease. Similarly, in [4], fMRI is used for analysis of epilepsy networks. Our modeling approach can play a critical role in the advancements of these fields. Our joint DCM and biophysics modeling can uniquely generate a brain function model that can reproduce both fMRI and electrophysiology data. Importantly, this approach can relate two types of data that have different spatial and temporal resolutions. This modeling approach can be a powerful tool in interpreting experimental data from different techniques and testing neuroscience hypotheses.

Example 4

BOLD fMRI and Electrophysiology Data

Functional magnetic resonance imaging (fMRI) is a neuroimaging method through which one can monitor the temporal changes in brain activity, non-invasively and at a large scale. It is has shown a tremendous success as a functional neuroimaging method in the past three decades and found use in both clinical and cognitive neuroscience [9]. In 1992 paper [1], authors propose an MRI method that allows us to image the temporal changes in brain activity by detecting blood oxygenation level in MRI. This paper marks the birth of fMRI through the detection of blood oxygen-level dependent (BOLD) signals. The phenomena underlying these signals is the oxygen requirement of neurons.

With periodically taken images, one can extract the activity of each voxel through the course of a scan. Once an fMRI scan is complete, what we have is a 4-D signal where the 4th dimension is time. We then anatomically mask this tensor to select regions of interest and perform dimensionality reduction on selected regions. We calculate the mean time series over each region to represent them with a single time series. In our method BOLD fMRI signals are one of the sources of the data that we use for modeling.

Electrophysiology techniques study the electrical properties, usually the voltage or current changes, of neurons. Popular noninvasive electrophysiology techniques include electroencephalogram (EEG) and magnetoencephalography (MEG), and invasive techniques such as intracellular, patch-clamping and extracellular recordings, which have been proven successful on collecting high temporal resolution data [5][18][11]. In our present study, we used spike trains collected from extracellular recordings. One advantage of electrophysiology is that recently it has been combined with cutting-edge techniques such as multiphoton microscopy and optogenetics. In our work, we used data from optogenetics fMRI, which enables researchers to excite or inhibit specific neurons using light, thus giving researchers unprecedented high spatial and temporal resolutions[13]. By recording the electrical activity surrounding a neuron that has been stimulated or inhibited it is possible to establish a direct link between a neuron's excitability and the responses in downstream/associated cells.

In summary, our method uses the non-invasive imaging technique fMRI to monitor temporal changes in brain regions of interest through a proxy called BOLD signal, and electrophysiology data to study the behaviors of specific neurons and associated mechanisms.

Example 5

Effective Connectivity and Dynamic Causal Modeling (DCM)

DCM is a Bayesian generative modeling paradigm which can model the causal relations in the brain comprehensively [6],[7]. It takes into account neuronal dynamics, modulatory and/or excitatory inputs and observational method (BOLD fMRI, EEG/MEG etc.), all at once. Hence, it is considered one of the most biologically plausible and technically advanced modeling methods [17]. Aim of DCM is to estimate the coupling among brain areas and their dependence on the experimental context, as well as finding model evidences to compare different hypothesis. The paper mentioned in the results part also utilizes this technique an can be found in [2].

DCM uses a state space system to model brain dynamics. There exist two sets of equations that govern this system, namely evolution and observation equations given in (1).

$$\dot{x}(t) = f(x(t), u(t); \theta_f) + w(t; \theta_w) \tag{1}$$

$$y(t) = g(x(t), u(t); \theta_g) + \epsilon(t, \theta_\epsilon)$$

The time series x(t) is the neuronal activity, u(t) is the input stimuli and y(t) is the observed signal. w(t) is state noise and E(t) is observation noise. Function g(.) is the observation model and changes with respect to the imaging method, whereas function f(.) is given as follows:

$$\dot{x}(t) = Ax(t) + u^T(t)Bx(t) + Cu(t) \tag{2}$$

Here, matrix A represents the effective connectivity strengths, as it defines the change in neuronal activity in a region in terms of current activity in all regions. This matrix is generally the main goal in a model fitting task. Matrix B and C are in the model to reflect the effect of inputs on the dynamics. Matrix B governs the connectivity modulation effect of inputs whereas matrix C models the direct contribution of an input to the dynamics.

There are several different types of DCM's in the literature. Classical DCM [6] assumes no state noise where as in stochastic DCM (sDCM) [14] state noise is utilized to account for uncertainty due to neighboring regions. Spectral DCM [7] is another paradigm that assumes state noise but in this approach model fitting is performed over the cross spectra of system and this makes it a useful model for resting state modeling. Dynamic effective connectivity (or dynamic DCM) [16] is also one of the approaches that we use in our method where on temporal changes in connectivity strengths are investigated. In our method we are able to use any type of DCM for one side of the joint modeling.

Inversion of DCM

DCM is a Bayesian modeling approach, meaning that its parameters are treated not as constants to be found but as distributions to be estimated, i.e. random variables. Therefore, what we are interested is p(θ/y, m), i.e. the posteriors, where θ is union of all parameters to be estimated and m is the model hypothesis we use. A model hypothesis in the DCM context can be seen as a particular choice of f, g and E and their respective priors. To exemplify, there are DCM's that use non-linear evolution functions [19] and some other models that have two neuronal states [15]. A choice therefore is referred to as a model in this context.

During the inversion, due to the Bayesian nature of the approach, we need to use priors. Choice of priors is actually an important consideration for proper modeling. Some of the parameters allow the use of information from previous neuroscience studies (such as hemodynamic priors) whereas for others we can only hypothesize a support set (such as A). In the latter type, we only make a binary decision about the existence of the parameter(i.e. whether its posterior will be non-zero). If it's set to zero posterior will have zero mean and variance.

Inversion of a DCM model is based on calculating model evidence p(y/m), which is the probability of observing the data given a model. Analytical calculation of model evidence is often intractable, therefore a common method to use for inversion is variational Bayes approach.

In this variational method, our task is to iteratively update a distribution called variational distribution (denoted by q(θ)). Log model evidence can be written as follows:

$$\ln p(y/m) = KL(q(\theta)//p(\theta/y, m)) + F(q(\theta), y) \tag{3}$$

Since we cannot know p(θ/y, m), first term cannot be calculated. But due to the properties of KL divergence we know that it is non-negative and the second term therefore constitutes a lower bound to the model evidence. Thus, the best estimate instead of maximizing the log model evidence is maximizing what's called negative free energy.

$$\ln p(y/m) \approx F(q(\theta, y)) = (\ln p(y/\theta, m))q - KL(q(\theta)//p(\theta/m)) \tag{4}$$

Here, q(θ) is the variational distribution which is also an approximation to the posterior distribution and KL(.) is the operation of Kullbeck-Leibler divergence. First term stands for the accuracy whereas second one has the complexity interpretation (since it measures the deviation from prior distribution). The lower bound mentioned above holds with equality if q*(θ)=p(θ/y, m). In DCM we also make an assumption about the distribution of parameters; they are assumed to be distributed normally. This assumption is called Laplace approximation and we reflect it in the prior distribution p(θ/m).

To summarize, our problem can be framed as follows:

$$\max_{q(\theta)}(\ln p(y/\theta, m))q - KL(q(\theta)//p(\theta/m)) \tag{5}$$

The solution to this problem is through an iterative method called Expectation Maximization(EM). EM is a steepest descent algorithm based on Jacobian calculations and a common tool in variational analysis. Once the algorithm converges, it returns the resultant model evidence and the variational distribution that results in that value. As stated before, this distribution is an approximation for the posterior distribution of parameters. A maximum a posteriori (MAP) estimation on those distribution would yield parameter estimates that we are looking for.

Biophysics Modeling Approach

Modeling based on the biophysics attributes of neurons and brain regions is another major neural modeling method. The main advantage of such an approach is that the models can reflect brain behaviors on different scales and resolutions.

At least one prior model should be built based on experimental results and hypothesis for testing. The prior model usually consists of two parts: structural model and neuronal model. The structural model determines the brain regions that are hypothetically involved in the process of interest and the regional connections; the neuronal model expands each region into a group of neuronal units to reflect detailed biophysical mechanisms. In our joint DCM and biophysics modeling process, the structural model is also the prior model for DCM analysis. The neuronal model first describes the firing pattern of a single neuron, typically by differential equations [22][12]. Other biophysics attributes sometimes are also described, such as self-connectivity, neuronal types, receptors, inputs and outputs topological structures, etc.[10][21].

In our example study, we used the neuronal model described in Hill and Tononi (Modeling sleep and wakefulness in the thalamocortical system. Journal of Neurophysiology, 93(3):1671-1698, 2005; herein incorporated by reference in its entirety). One may choose other types of biophysics models. The simulated neuron emits a single spike if it is not refractory and the membrane potential passes the threshold. One neuron enters refractory period after spike emission for a constant time and during this period no new spikes can be generated. The membrane potential V is governed by $$\frac{dV}{dt} = \frac{-g_{Na}(V - E_{Na}) - g_K(V - E_K) + I_{syn} + I_{int}}{\tau_m - I_{re}} \tag{6}$$

The $g_{Na}$ and $g_K$ are Na and K constant leak conductances. $E_{Na}$ and $E_K$ are reversal potentials, which are assumed to be constants. $I_{syn}$ is the synaptic currents from other neurons. $I_{int}$ is the intrinsic current. $I_{re}$ is a re-polarizing current that is only active during refractory periods. $\tau_m$ is the time constant.

The outputs of the biophysical model are electrophysiology data, either in the forms of EEG/MEG style time series or single neuron recording style spike trains depending on the chosen type of neuronal model. In our example study the outputs are spike trains from single neurons. The simulated electrophysiology data then can be converted into fMRI BOLD time series using hemodynamic function. A comprehensive model that explains this process is provided by Buxton et al.[3], with the name "balloon model". In this model, the complex relation between blood oxygen level and neuronal activity is proposed as a system of differential equations. The exact set of equations can be found in (7) where x is the neuronal activity, s is vasodilatory signal, f is blood inflow, κ is signal decay constant, γ is feedback regulatory constant, v is blood volume in a brain region, $f_{out}$ is blood outflow, r is mean transit time of blood, a is vessel stiffness, q is deoxyhemoglobin content and $E_0$ is oxygen extraction fraction at rest.

$$\dot{s}(t) = x(t) - \kappa s(t) - \gamma(f(t) - 1) \tag{7}$$

$$\dot{f}(t) = s(t)$$

$$\dot{v}(t) = \frac{1}{\tau} f(t) - \frac{1}{\tau} f_{out}(t)$$

$$f_{out}(t) = v(t)^{\frac{1}{\alpha}}$$

$$\dot{q}(t) = \frac{1}{\tau}\left[\frac{1-(1-E_0)^{\frac{1}{f(t)}}}{E_0} f(t) - \frac{q(t)}{v(t)} v(t)^{\frac{1}{\alpha}}\right]$$

Under these underlying dynamics, observed signal y(t), i.e. the time course of a voxel intensity, is proposed to be:

$$y(t) \approx V_0\left[k_1(1-q(t)) + k_2\left(1 - \frac{q(t)}{v(t)}\right) + k_3(1-v(t))\right] \tag{8}$$

where coefficients $k_1$, $k_2$ and $k_3$ are examined in [20] and they are a combination of scanning and biological parameters. In this model, one can see that neuronal activity causes blood vessels to dilate, which in return increases the blood inflow. Net flow directly effects the blood volume and final two relations show the tight relation between blood flow, volume and deoxyhemoglobin content. This model forwards the neuronal activity to fMRI BOLD signal changes. Thus, one can directly compare simulation and experimental results by comparing the fMRI time series and DCM results from simulations with those from experiments, and modify the prior model accordingly or choose another prior model.

Software

Prof. Karl Friston and his colleagues at Wellcome Centre for Human Neuroimaging, University College London have released a MATLAB toolbox named SPM (Statistical Parametric Mapping) that can be used for many functional neuroimaging applications [8]. DCM inversion and analysis is one the capabilities of this toolbox and it is commonly used in DCM literature. Our method is based on their toolbox.

REFERENCES

[1] Peter A Bandettini, Eric C Wong, R Scott Hinks, Ronald S Tikofsky, and James S Hyde. Time course epi of human brain function during task activation. *Magnetic resonance in medicine,* 25(2):390-397, 1992.

[2] David Bernal-Casas, Hyun Joo Lee, Andrew J Weitz, and Jin Hyung Lee. Studying brain circuit function with dynamic causal modeling for optogenetic fmri. *Neuron,* 93(3):522-532, 2017.

[3] Richard B Buxton, Eric C Wong, and Lawrence R Frank. Dynamics of blood flow and oxygenation changes during brain activation: the balloon model. *Magnetic resonance in medicine,* 39(6):855-864, 1998.

[4] ManKin Choy, Ben A Duffy, and Jin Hyung Lee. Optogenetic study of networks in epilepsy. *Journal of neuroscience research,* 95(12):2325-2335, 2017.

[5] Fernando Lopes da Silva. EEG and MEG: relevance to neuroscience. *Neuron,* 80(5):1112-1128, 2013.

[6] Karl J Friston, Lee Harrison, and Will Penny. Dynamic causal modeling. *Neuroimage,* 19(4):1273-1302, 2003.

[7] Karl J. Friston, Joshua Kahan, Bharat Biswal, and Adeel Razi. A DCM for resting state fMRI. *NeuroImage,* 94:396-407, 2014.

[8] K. J. Friston, J. Ashburner, S. J. Kiebel, T. E. Nichols, and W. D. Penny, editors. *Statistical Parametric Mapping: The Analysis of Functional Brain Images*. Academic Press, 2007.

[9] Gary H Glover. Overview of functional magnetic resonance imaging. *Neurosurgery Clinics,* 22(2):133-139, 2011.

[10] Sean Hill and Giulio Tononi. Modeling sleep and wakefulness in the thalamocortical system. *Journal of neurophysiology,* 93(3):1671-1698, 2005.

[11] Donald R Humphrey and Edward M Schmidt. Extracellular single-unit recording methods. In *Neuro-physiological techniques*, pages 1-64. Springer, 1990.

[12] Eugene M Izhikevich. Simple model of spiking neurons. *IEEE Transactions on neural networks,* 14(6):1569-1572, 2003.

[13] Hyun Joo Lee, Andrew J Weitz, David Bernal-Casas, Ben A Duffy, ManKin Choy, Alexxai V Kravitz, Anatol C Kreitzer, and Jin Hyung Lee. Activation of direct and indirect pathway medium spiny neurons drives distinct brain-wide responses. *Neuron,* 91(2):412-424, 2016.

[14] Baojuan Li, Jean Daunizeau, Klaas E. Stephan, Will Penny, Dewen Hu, and Karl Friston. Generalised filtering and stochastic DCM for fMRI. *NeuroImage,* 58(2):442-457, 2011.

[15] Andr'e C Marreiros, Stefan J Kiebel, and Karl J Friston. Dynamic causal modeling for fmri: a two-state model. *Neuroimage,* 39(1):269-278, 2008.

[16] Hae-Jeong Park, Karl J Friston, Chongwon Pae, Bumhee Park, and Adeel Razi. Dynamic effective connectivity in resting state fmri. *Neuroimage,* 180:594-608, 2018.

[17] Stephen M Smith. The future of fmri connectivity. *Neuroimage,* 62(2):1257-1266, 2012.

[18] Harald Sontheimer and Christopher B Ransom. Whole-cell patch-clamp recordings. In *Patch-Clamp Analysis*, pages 35-67. Springer, 2002.

[19] Klaas Enno Stephan, Lars Kasper, Lee M Harrison, Jean Daunizeau, Hanneke E M den Ouden, Michael Breakspear, and Karl J Friston. Nonlinear dynamic causal models for fmri. *Neuroimage,* 42(2):649-662, 2008.

[20] Klaas Enno Stephan, Nikolaus Weiskopf, Peter M Drysdale, Peter A Robinson, and Karl J Friston. Comparing hemodynamic models with dcm. *Neuroimage,* 38(3): 387-401, 2007.

[21] M A Tagamets and B Horwitz. Integrating electrophysiological and anatomical experimental data to create a large-scale model that simulates a delayed match-to-sample human brain imaging study. *Cerebral cortex* (New York, NY: 1991), 8(4):310-320, 1998.

[22] Hugh R Wilson and Jack D Cowan. Excitatory and inhibitory interactions in localized populations of model neurons. *Biophysical journal,* 12(1):1-24, 1972.

What is claimed is:

1. A method of detecting a brain response to a treatment of a neurological disease or disorder in a subject, the method comprising:

a) treating the neurological disease or disorder in the subject by administering a therapeutic for treatment of the neurological disease or disorder to the subject, delivering stimulation with an electrical current or magnetic field to the brain of the subject, or optogenetically stimulating the brain of the subject using light;

b) acquiring functional neuroimaging data of neural activity in one or more regions of interest in a brain of the subject before and after said treating the neurological disease or disorder in the subject;

c) acquiring experimental electrophysiology data for one or more neurons in said one or more regions of interest in the brain of the subject before and after said treating the neurological disease or disorder in the subject;

d) fitting the functional neuroimaging data of the neural activity acquired before said treating the neurological disease or disorder in the subject to a first dynamic causal model (DCM), and fitting the functional neuroimaging data of the neural activity acquired after said treating the neurological disease or disorder in the subject to a second DCM;

e) calculating neural inter-regional and intra-regional connectivity strength estimates from the first DCM and the second DCM;

f) fitting the experimental electrophysiology data acquired before said treating the neurological disease or disorder in the subject to a first biophysics model, wherein the first biophysics model uses the inter-regional and intra-regional connectivity strength estimates calculated from the first DCM to estimate effects of inter-regional and intra-regional neural activities on rates of change of neural activities of neuronal populations included in the first biophysics model, and wherein the first biophysics model simulates synthetic electrophysiology data, and fitting the experimental electrophysiology data acquired after said treating the neurological disease or disorder in the subject to a second biophysics model, wherein the second biophysics model uses the inter-regional and intra-regional connectivity strength estimates calculated from the second DCM to estimate effects of inter-regional and intra-regional neural activities on rates of change of neural activities of neuronal populations included in the second biophysics model, and wherein the second biophysics model simulates synthetic electrophysiology data; wherein said fitting the experimental electrophysiology data acquired before said treating the neurological disease or disorder in the subject further comprises comparing the synthetic electrophysiology data simulated from the first biophysics model to the experimental electrophysiology data acquired before said treating the neurological disease or disorder in the subject and adjusting parameters of the first biophysical model iteratively until model convergence is reached with the experimental electrophysiology data acquired before said treating the neurological disease or disorder in the subject; and wherein said fitting the experimental electrophysiology data acquired after said treating the neurological disease or disorder in the subject further comprises comparing the synthetic electrophysiology data simulated from the second biophysics model to the experimental electrophysiology data acquired after said treating the neurological disease or disorder in the subject and adjusting parameters of the second biophysical model iteratively until model convergence is reached with the experimental electrophysiology data acquired after said treating the neurological disease or disorder in the subject;

g) detecting the brain response to the treatment based on comparing the first biophysical model to the second biophysical model to detect a difference between the first biophysical model and the second biophysical model to identify a change in the neural activity in the subject after administering the treatment for the neurological disease or disorder compared to the neural activity in the subject before the treatment for the neurological disease or disorder;

h) displaying a depiction of the brain including the one or more regions of interest wherein each region of interest of the one or more regions of interest in the depiction of the brain are associated with a corresponding chart illustrating the synthetic electrophysiology data generated by the first biophysics model for the region of interest and the synthetic electrophysiology data generated by the second biophysics model for the region of interest.

2. The method of claim 1, wherein said functional neuroimaging data comprises functional magnetic resonance imaging (fMRI) data, positron emission tomography (PET) data, functional near-infrared spectroscopy (fNIRS) data, single-photon emission computed tomography (SPECT) data, or functional ultrasound imaging (fUS) data.

3. The method of claim 1, wherein the experimental electrophysiology data comprises electroencephalography (EEG), magnetoencephalography (MEG), or patch-clamping data.

4. The method of claim 1, wherein said one or more regions of interest are in cerebrum, cerebellum, brainstem, basal ganglia, striatum, medulla, pons, hypothalamus, thalamus, superior colliculus, cerebral cortex, neocortex, allocortex, hippocampus, olfactory bulb, frontal lobe, temporal lobe, parietal lobe, occipital lobe, caudate-putamen, external globus pallidus, internal globus pallidus, subthalamic nucleus, substantia nigra, or motor cortex regions of the brain.

5. The method of claim 1, wherein the one or more neurons are unipolar neurons, bipolar neurons, multipolar neurons, Golgi I neurons, Golgi II neurons, anaxonic neurons, pseudounipolar neurons, interneurons, motor neurons, sensory neurons, afferent neurons, efferent neurons, cholinergic neurons, GABAergic neurons, glutamatergic neurons, dopaminergic neurons, serotonergic neurons, histaminergic neurons, Purkinje cells, spiny projection neurons, Renshaw cells, or granule cells, or a combination thereof.

6. The method of claim 1, wherein the functional neuroimaging data comprises data from optical imaging or multiphoton microscopy of the one or more regions of interest in the brain of the subject.

7. The method of claim 1, further comprising detecting a change in brain function in the subject compared to brain function of a control subject based on comparing the first DCM to a reference DCM determined from functional neuroimaging data of the control subject to detect a difference in the brain function between the first DCM and the reference DCM or comparing the first biophysics model to a reference biophysics model determined from experimental electrophysiology data of the control subject to detect a difference in the brain function between the first biophysics model and the reference biophysics model to identify the change in brain function in the subject compared to the brain function of the control subject.

8. The method of claim 7, further comprising identifying a neural circuit involved in pathological changes associated with the neurological disease or disorder based on detecting a difference in the neural circuit involved in the pathological changes in the first biophysics model and the reference biophysics model determined from the experimental electrophysiology data of the control subject.

9. The method of claim 1, wherein the DCM is classical DCM, stochastic DCM, spectral DCM, or dynamic DCM.

10. The method of claim 1, further comprising:

acquiring functional neuroimaging data of neural activity in the one or more regions of interest in the brain of the subject while the subject is in a resting state and while the subject is performing a task or responding to a stimulus;

acquiring experimental electrophysiology data for the one or more neurons in the one or more regions of interest in the brain of the subject while the subject is in the resting state and while the subject is performing the task or responding to the stimulus;

fitting the functional neuroimaging data of the neural activity acquired while the subject is in the resting state to a third DCM, and fitting the functional neuroimaging data of the neural activity acquired while the subject is performing the task or responding to the stimulus to a fourth DCM;

calculating neural inter-regional and intra-regional connectivity strength estimates from the third DCM and the fourth DCM;

fitting the experimental electrophysiology data acquired while the subject is in the resting state to a third biophysics model, wherein the third biophysics model uses the inter-regional and intra-regional connectivity strength estimates calculated from the third DCM to estimate effects of inter-regional and intra-regional neural activities on rates of change of neural activities of neuronal populations included in the third biophysics model, and wherein the third biophysics model simulates synthetic electrophysiology data, and fitting the experimental electrophysiology data acquired while the subject is performing the task or responding to the stimulus to a fourth biophysics model, wherein the fourth biophysics model uses the inter-regional and intra-regional connectivity strength estimates calculated from the fourth DCM to estimate effects of inter-regional and intra-regional neural activities on rates of change of neural activities of neuronal populations included in the fourth biophysics model, and wherein the fourth biophysics model simulates synthetic electrophysiology data; wherein said fitting the experimental electrophysiology data acquired while the subject is in the resting state comprises comparing the synthetic electrophysiology data simulated from the third biophysics model to the experimental electrophysiology data acquired while the subject is in the resting state and adjusting parameters of the third biophysical model iteratively until model convergence is reached with the experimental electrophysiology data acquired while the subject is in the resting state, and wherein said fitting the experimental electrophysiology data acquired while the subject is performing the task or responding to the stimulus comprises comparing the synthetic electrophysiology data simulated from the fourth biophysics model to the experimental electrophysiology data acquired while the subject is performing the task or responding to the stimulus, and adjusting parameters of the fourth biophysical model iteratively until model convergence is reached with the experimental electrophysiology data acquired while the subject is performing the task or responding to the stimulus; and identifying a neural circuit involved in performing the task or responding to the stimulus based on comparing the third biophysical model to the fourth biophysical model to detect a difference in the neural circuit between the third biophysical model and the fourth biophysical model to identify a change in the neural circuit in the subject after performing the task or responding to the stimulus compared to while the subject is in the resting state.

* * * * *